United States Patent
Hamza et al.

(10) Patent No.: US 10,227,320 B2
(45) Date of Patent: Mar. 12, 2019

(54) COMPOUNDS FOR TREATING PARASITIC INFECTIONS

(71) Applicants: University of Maryland, College Park, College Park, MD (US); University of Maryland, Baltimore, Baltimore, MD (US)

(72) Inventors: Iqbal Hamza, Kensington, MD (US); Fengtian Xue, Potomac, MD (US)

(73) Assignees: University of Maryland, College Park, College Park, MD (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 15/571,879

(22) PCT Filed: May 6, 2016

(86) PCT No.: PCT/US2016/031234
§ 371 (c)(1),
(2) Date: Nov. 6, 2017

(87) PCT Pub. No.: WO2016/179505
PCT Pub. Date: Nov. 10, 2016

(65) Prior Publication Data
US 2018/0118704 A1    May 3, 2018

Related U.S. Application Data

(60) Provisional application No. 62/157,870, filed on May 6, 2015.

(51) Int. Cl.
| | | |
|---|---|---|
| C07D 307/88 | (2006.01) |
| A61K 31/343 | (2006.01) |
| C07D 307/90 | (2006.01) |
| A01N 37/22 | (2006.01) |
| A01N 43/12 | (2006.01) |
| A01N 43/40 | (2006.01) |
| A01N 43/78 | (2006.01) |
| C07C 237/40 | (2006.01) |
| C07D 307/87 | (2006.01) |
| C07D 405/12 | (2006.01) |
| C07D 417/12 | (2006.01) |

(52) U.S. Cl.
CPC .......... *C07D 307/90* (2013.01); *A01N 37/22* (2013.01); *A01N 43/12* (2013.01); *A01N 43/40* (2013.01); *A01N 43/78* (2013.01); *A61K 31/343* (2013.01); *C07C 237/40* (2013.01); *C07D 307/87* (2013.01); *C07D 405/12* (2013.01); *C07D 417/12* (2013.01)

(58) Field of Classification Search
CPC .......................... C07D 307/88; A61K 31/343
See application file for complete search history.

(56) References Cited

U.S. PATENT DOCUMENTS

| | | |
|---|---|---|
| 3,519,678 A | 7/1970 | Farrington et al. |
| 2005/0165068 A1 | 7/2005 | Lepape |
| 2006/0206946 A1 | 9/2006 | Hamza |
| 2007/0099919 A1 | 5/2007 | Rana |
| 2009/0305886 A1 | 12/2009 | Langewald et al. |
| 2010/0062937 A1 | 3/2010 | Wada et al. |
| 2013/0210915 A1 | 8/2013 | Wadell et al. |

OTHER PUBLICATIONS

Sanchez-Sancho, CAPLUS abstract of N-(2-Aminoethyl)-4-methylbenzenesulfonamide, Doc No. 164:555934 (Year: 2010).*
PubChem-CID 2327258, Create Date: Jul. 15, 2005, pp. 1-12.

* cited by examiner

*Primary Examiner* — Rebecca L Anderson
*Assistant Examiner* — Karen Cheng
(74) *Attorney, Agent, or Firm* — Hodgson Russ LLP

(57) ABSTRACT

Compounds and compositions comprising them are provided. The compounds and compositions are useful for inhibiting transport of heme across membranes in parasitic heme auxotrophic organisms, thereby limiting their growth or killing the parasites.

2 Claims, 6 Drawing Sheets

COMPOUNDS FOR TREATING PARASITIC INFECTIONS

CROSS REFERENCE TO RELATED APPLICATIONS

This application claims priority to U.S. patent application No. 62/157,870, filed May 6, 2015, the disclosure of which is incorporated herein by reference.

FIELD

The present disclosure relates generally to compounds and methods for using the compounds to kill or inhibit the growth of parasites, and more specifically for killing or inhibiting growth of parasites that are heme auxotrophs.

BACKGROUND

Over 1.4 billion people across the globe are affected by Neglected Tropical Diseases (NTD)—a group of thirteen parasitic and bacterial infections. NTD include the soil-transmitted helminthiasis, schistosomiasis, lymphatic filariasis, onchocerciasis, and trachoma, as well as trypanosomiasis and leishmaniasis. Often, individuals are infected with multiple NTD agents simultaneously. Currently, the effectiveness of all agents used to treat parasites is diminished by four factors: (a) resistance develops and spreads rapidly, (b) parasites do not actively transport drugs into their bodies, (c) many drugs (eg: anthelminthics) are effective only during certain developmental stages of the parasite, and (d) drugs tend to act on a specific type of parasite and are ineffective in controlling other parasite populations.

Although these are devastating diseases of global concern, their neglected status relative to other health concerns has resulted in a limited arsenal of therapeutic compounds for their treatment [Chatelain E, et al. Drug Des Devel Ther 2011, 5:175-181]. The trypanosomatid parasites *L. major* and *L. amazonensis* are causative agents of human cutaneous leishmaniasis in the Old World and New World, respectively. Combined, these two species are responsible for an estimated 2 million new infections annually with ~350 million people living in areas of active parasite transmission. In many regions of the world, treatment of leishmaniasis still relies on toxic drugs such as pentavalent antimony, which requires high doses and lengthy courses of treatment, and alternative drugs are still costly and not widely available in endemic areas. This situation, combined with the recent increase in *Leishmania* infections in urban areas, highlights the urgent need for identification of essential pathways in these organisms that can be targeted by new drugs with lower toxicity.

It was previously demonstrated that the free-living roundworm *C. elegans* and parasitic nematodes cannot synthesize heme, an iron-containing heterocyclic organic ring structure, but instead acquires heme from either their environment or their host to survive and reproduce PMID: 15767563. It is generally accepted that parasites exhibit distinct adaptations that allow them to acquire nutrients unidirectionally from the host to sustain their growth and reproduction. An example of such an adaptation would be the uptake of heme which the parasite cannot produce but is synthesized by all vertebrates (hosts) via a highly conserved multi-step pathway [Hamza I, et al. Biochim Biophys Acta 2012, 1823(9): 1617-1632]. This unusual requirement for external heme is also found in single-celled parasites such as *Trypanosomes* and *Leishmania* [Hamza I, et al. Biochim Biophys Acta 2012, 1823(9):1617-1632; Chang C S, et al. Mol Biochem Parasitol 1985, 16(3):267-276]. Thus, drugs that target heme transport pathways unique to the parasite and not shared by its mammalian host offers great therapeutic potential. A drug that blocks heme transport or that enters the parasite via a high affinity and essential heme uptake pathway can be a highly effective broad-spectrum therapeutic agent, since such transport mechanisms are likely to have similarities across multiple parasite species. Parasites that limit transport or become resistant to the drug will indirectly also limit heme uptake, suffering impaired growth and development, and this approach could be applied to the treatment of infections caused by a diverse group of parasites, including intestinal nematodes, lymphatic and cutaneous filarial nematodes, and the kinetoplastids *Leishmania* and *Trypanosoma*. Thus, there is an ongoing and unmet need for compounds that selectively inhibit targets that are exclusively expressed by the parasites, as opposed to their hosts, and for methods of using such compounds to limit growth or kill such parasites. The present disclosure meets this need.

SUMMARY OF THE DISCLOSURE

The present disclosure provides compounds and compositions comprising them. The compounds and compositions are useful for inhibiting the transport of heme across membranes in parasitic heme auxotrophic organism, and thus can be used as agents for inhibiting the growth and/or killing the parasitic heme auxotrophic organisms.

The disclosure comprises methods and compounds, and compositions comprising the compounds, where the compounds have one of the following structures:

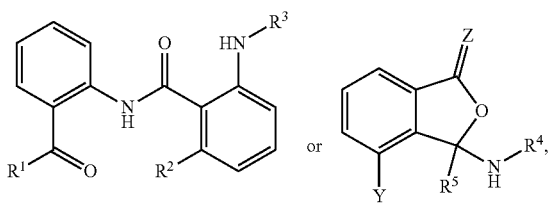

where $R^1$ is selected from the group consisting of —OH, —OMe, and —NHR$^6$, where $R^6$ is selected from the group consisting of $C_1$-$C_5$ alkyl, $C_3$-$C_6$ cycloalkyl, pyridine, and phenyl; $R^2$ is selected from the group consisting of —H, —F, —Cl, —OMe, and —OH; $R^3$ is selected from the group consisting of $C_4$-$C_6$ cycloalklyl, phenyl and pyridine; $R^4$ is selected from the group consisting of $C_1$-$C_8$ alkyl, $C_4$-$C_6$ cycloalklyl, substituted or unsubstituted phenyl, substituted or unsubstituted alkyl amine, substituted or unsubstituted naphthyl and heterocyclic; $R^5$ is selected from the group consisting of

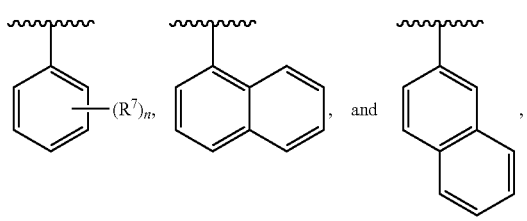

$R^7$ is independently selected from the group consisting of halogen, phenyl, and alkyl; n equals 0-5, Y is —H, —F, —Cl, or -Me; and Z is O or $NR^8$ where $R^8$ is

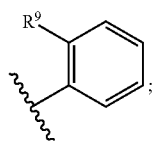

and $R^9$ is selected from the group consisting of —OMe and —F.

In an embodiment, the compound has the following structures:

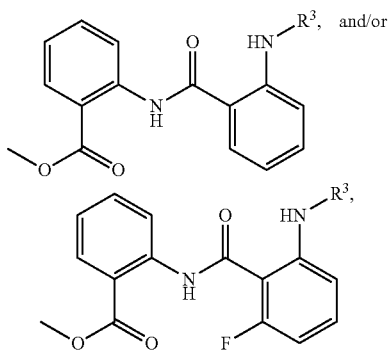

where $R^3$ is selected from the group consisting of $C_4$-$C_6$ cycloalkyl, phenyl and pyridine.

In an embodiment, the compound has the following structures:

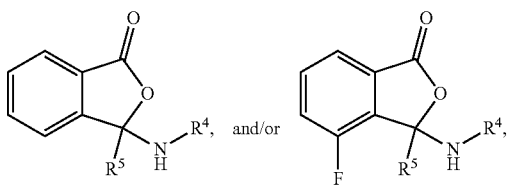

where $R^4$ is selected from the group consisting of $C_1$-$C_8$ alkyl, $C_4$-$C_6$ cycloalklyl, substituted phenyl, substituted or unsubstituted alkyl amine, naphthyl, substituted naphthyl and heterocyclic; and $R^7$ is selected from the group consisting of H, halogen, phenyl, and alkyl.

In an embodiment, the compound has the following structures:

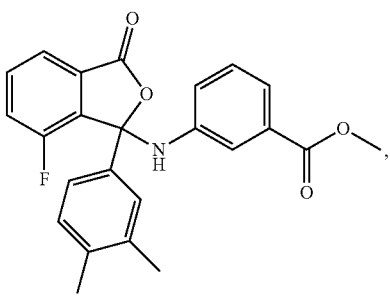

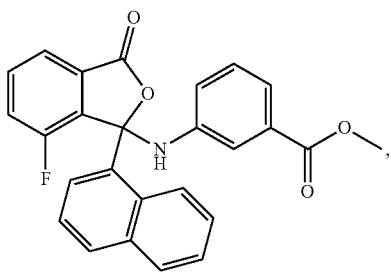

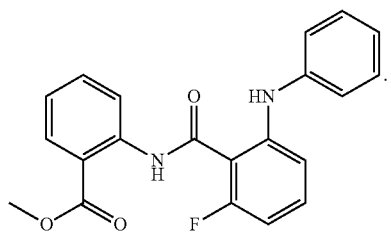

In one implementation the disclosure comprises a method for inhibiting transport of heme across a membrane in a parasitic heme auxotrophic organism comprising contacting the parasitic organism with an effective amount any of the foregoing compounds. In certain implementations, inhibiting the transport of heme is lethal to the parasitic heme auxotrophic organism. In non-limiting examples the parasitic heme auxotrophic organism is *Leishmania*, which can be targeted as, for example, a promastigote or an amastigote. The compositions and methods are expected to be suitable for prophylaxis and/or therapy for human and veterinary indications.

The disclosure also includes kits comprising any one or combination of the compounds described herein, and may further include printed or digitized instructions and/or an indication that compounds are for use in inhibiting the growth of or killing a parasitic heme auxotrophic organism, or for treating an individual for an infection by a parasitic heme auxotrophic organism.

DETAILED DESCRIPTION

Figure 1:
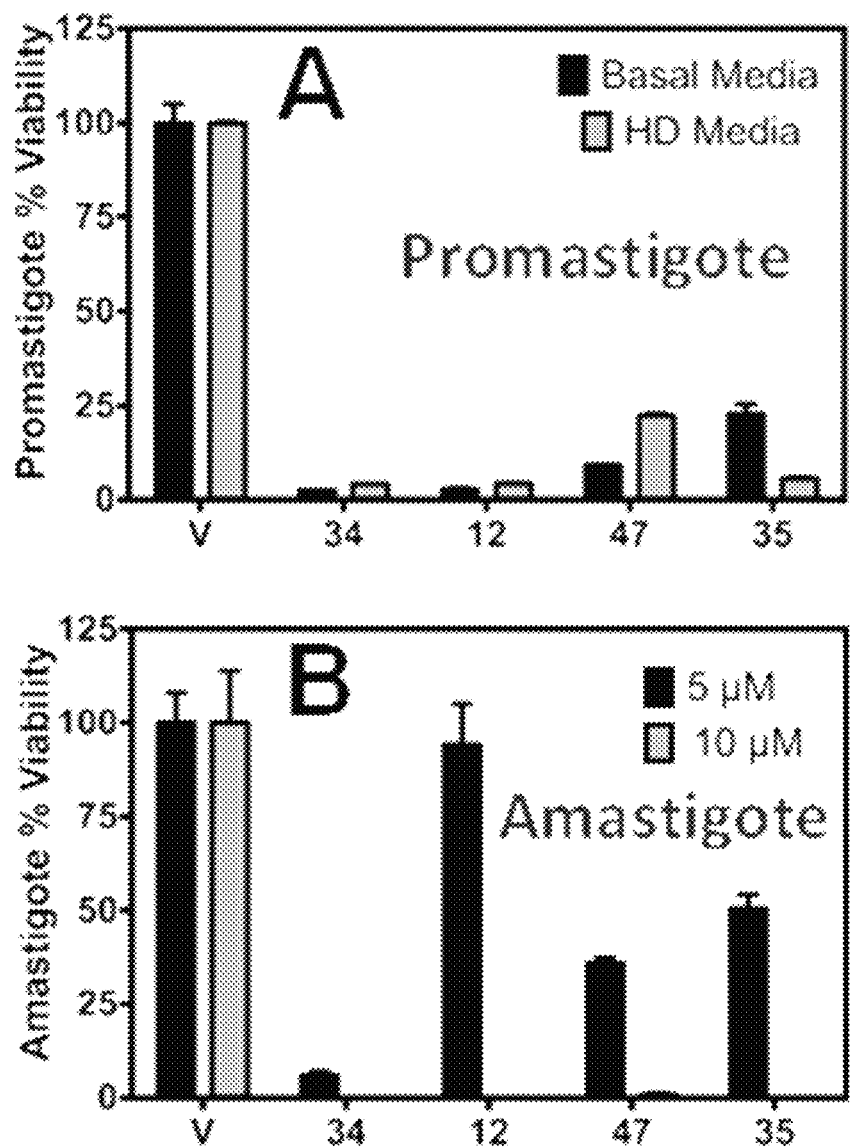
FIG. 1. Compounds identified as LHR1 inhibitors decrease parasite viability. (A) Log phase axenic promastigotes were incubated in basal or heme depleted (HD) M199 media for 48 h (h=hour(s)) in the presence of 50 μM of compounds indicated on the x-axis in 1% DMSO (V). (B) Axenic amastigotes were incubated in 5 μM or 10 μM of the indicated compounds in 1% DMSO for 72 h. Viability (%) was quantitated using Alamar blue compared to DMSO (V).
Figure 2:
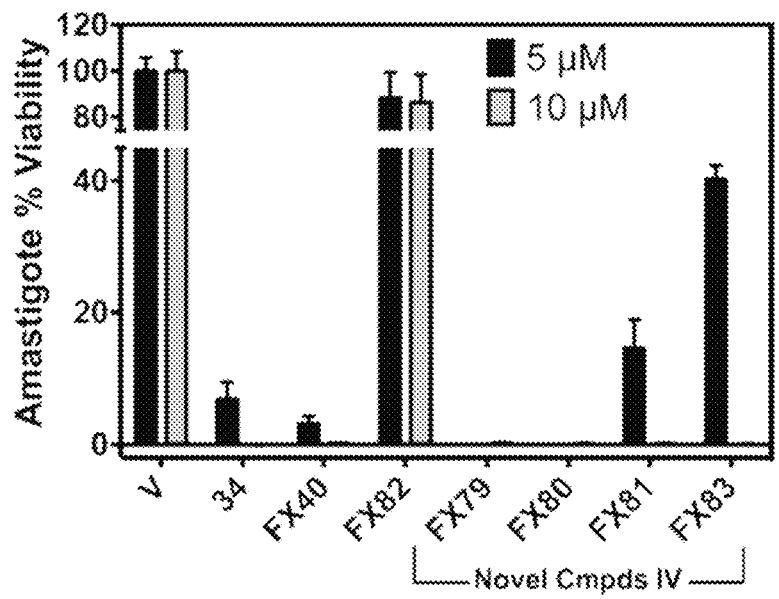
FIG. 2. Axenic *L. amazonensis* amastigotes are sensitive to Cmpd #34 and novel derivatives. Axenic amastigotes were incubated in 5 μM or 10 μM of the indicated compounds in 1% DMSO (V) for 72 h. Viability was quantified using Alamar Blue.
Figure 3:
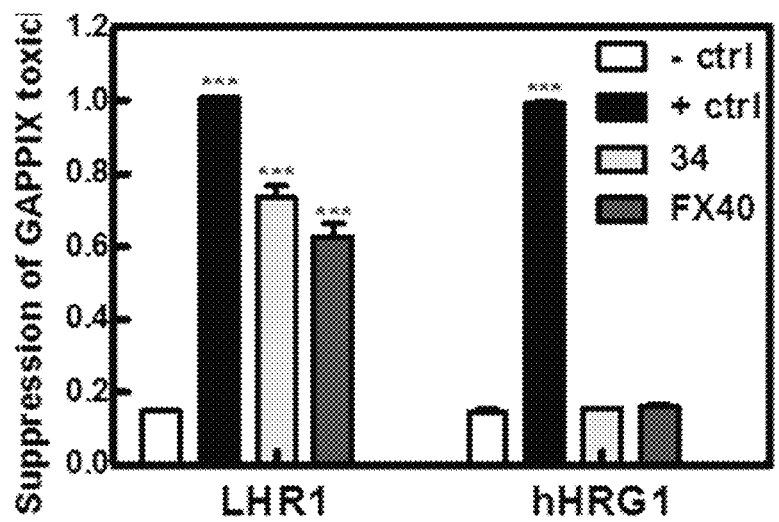
FIG. 3. Cmpd #34 and FX40 specifically inhibit LHR1, but not human HRG1, mediated heme uptake in yeast. Yeast cells expressing pGAL1-LHR1 or pGAL1-hHRG1 were incubated in growth medium containing 10 μM compounds and GaPPIX for 42 h. Cell growth was measured by absorbance at O.D. 600 and compared to negative control (DMSO, indicated by "V"), or positive control (0.2% glucose, indicated by "Glu"). ***$p<0.001$.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The present disclosure provides compounds, pharmaceutical compositions comprising the compounds, and methods of using the compounds for antagonizing one or more pathways required for the transport of heme. This therapeutic strategy was chosen based at least in part on the following observations: (a) heme is utilized in multiple, critical processes; (b) heme is required in all stages of development; (c) *Leishmania* and other parasitic heme auxotrophs cannot live without heme and actively ingest it; and (d) both humans and their parasites require heme, but the mechanisms used to fulfill this requirement differ between humans and their parasites.

In general, the disclosure is directed to killing or inhibiting the growth of parasitic organisms that acquire environmental heme, including but not necessarily limited to parasitic helminths, such as ascarids (*Ascaris*), filarias, hookworms, pinworms (*Enterobius*) and whipworms (*Trichuris trichiura*), and members of class Kinetoplastea, including but not necessarily limited to parasites of the genus *Trypanosoma*, such as *T. brucei* and *T. cruzi* and *Leishmania*, including all members of the *Leishmania* subgenuses.

In certain embodiments, the disclosure pertains to inhibiting the transport of heme across a membrane in a parasitic heme auxotrophic organism or in a heme prototroph, such as plasmodium. In embodiments, the disclosure comprises inhibiting the transport of heme across a membrane of a parasitic heme auxotrophic organism. In embodiments the organism that is present in a human or non-human animal. Thus, the disclosure includes human and veterinary therapeutic approaches. In embodiments, the parasitic heme auxotrophic organism is present in an insect or a plant. In embodiments, the parasitic heme auxotrophic organism is present in a cell. In embodiments, the disclosure comprises inhibiting the transport of heme across a membrane of a parasitic heme auxotrophic organism that is present in an insect, such as a fly, or in a mammalian cell, including but not necessarily limited to leukocytes, such as monocytes, neutrophils, macrophage, or hepatocytes. In embodiments, the infected cells are present in an organ in an individual, such as the liver or spleen or bone marrow or skin. In embodiments, the parasitic heme auxotrophic organism is an amastigote or a promastigote.

In a non-limiting aspect, the present disclosure uses *Leishmania* as a target parasitic heme auxotrophic organism to demonstrate utility of the compounds described herein. Thus, in embodiments, compounds of the disclosure are selective antagonists of one or more heme transporters in *Leishmania*. Without intending to be constrained by any particular theory, the heme transporter from *Leishmania* parasite is used as a non-limiting example of utility of the present compositions and methods according to the following rationale: (a) no satisfactory treatment available except antimonials which are toxic with serious side effects in humans; (b) single-celled protozoa that are genetically manipulatable for ectopic overexpression or gene knockouts; (c) fully sequenced and annotated genome; (d) and growth can be manipulated for pharmacologic assays in free-living (axenic), intracellular (inside macrophages) or in vivo (in mice/hamsters) stages.

Since previous to the present disclosure no effective drugs exist to treat leishmaniasis except antimonials which are highly toxic to humans, a cell-based, high throughput screen (HTS) of >200,000 compounds using growth assays in yeast was performed. As described below, the disclosure includes identification of several antagonists that specifically inhibit the heme transport function of the *Leishmania* LHR1 but not the corresponding human homolog (hHRG1). The identified compounds were used in part to design and synthesize the novel compounds described herein.

In embodiments, the disclosure comprises exposing *Leishmania* or other parasitic heme auxotrophs to one or more compounds of this disclosure such that is inhibited or they are killed. In certain approaches the method comprises reducing the amount of *Leishmania* promastigotes, such as in a sandfly, or comprises reducing the amount of *Leishmania* amastigotes. In one approach the disclosure includes administering to an individual in need thereof a composition comprising one or more of the compounds described herein.

This is expected to result in reducing the amount of *Leishmania* organisms in the individual, or in the eradication of *Leishmania* organisms from the individual. It is contemplated that the individual can be infected with any *Leishmania* strain, and can be diagnosed with or suspected of having any type of leishmaniasis, such as cutaneous leishmaniasis, or diffuse cutaneous leishmaniasis, or visceral leishmaniasis. The individual may be a human, or a non-human mammal, including but not necessarily limited to a canine.

The compounds of this disclosure can be combined with any pharmaceutically acceptable carrier, excipient, diluent and the like to obtain pharmaceutical compositions. Compositions comprising the compounds can be administered to an individual using any suitable route, dosage and formulation. In embodiments, the compositions are administered orally, parenterally, sublingually, transdermally, transmucosally, or topically. Parenteral administration includes, but is not limited to, intravenous, intraarterial, intraperitoneal, subcutaneous, and intramuscular routes. Administration of the compounds can be performed sequentially or concurrently with any other anti-infective compositions of matter and treatment modalities. Further, the disclosure encompasses combinations of the compounds of this disclosure with known anti-infective agents. In embodiments, the compounds of this disclosure can be used in conjunction with anti-infective agents which include but are not necessarily limited to liposomal amphotericin B, pentavalent antimonials, paromomycin, including topical paromomycin, miltefosine, fluconazole, itraconazole, and combinations thereof.

The disclosure includes pharmaceutically acceptable salts of the compounds disclosed herein.

The compounds can be provided in any suitable form, including in solutions, suspensions, emulsions, or as dry material for reconstitution prior to use, or in tablets, capsules, and the like. The compounds can be formulated for rapid or sustained release. The compounds can be combined with any suitable drug delivery vehicle, including but not necessarily limited to liposomal formulations, nanoparticle formulations, or other delivery vehicles that will be apparent to those skilled in the art given the benefit of the present disclosure.

The compounds can be provided as an article of manufacture, such as a kit, that includes, for example, a closed or sealed package that contains the compounds. In certain embodiments, the package can comprise one or more closed or sealed vials, bottles, or any other suitable packaging and/or containers for the sale, or distribution, or use of the compounds. The article of manufacture can include printed information. The printed information can be provided on a label, or on a paper insert, or it can be printed on the packaging material itself. The printed information can include information that identifies the compound, the amounts and types of other active and/or inactive ingredients, and instructions for taking the composition, such as the number of doses to take over a given period of time, and/or information directed to a pharmacist and/or another health care provider, such as a physician, or a patient. In embodiments the printed information includes an indication that the contents of the article of manufacture is for use in treating a parasitic infection, examples of which are described above.

With respect to the compounds of this disclosure, the following description is pertinent. In particular, as used herein, the term "alkyl" group, unless otherwise stated, refers to branched or unbranched hydrocarbons. Examples of such alkyl groups include methyl groups, ethyl groups, propyl groups, butyl groups, isopropyl groups, sec-butyl, tert-butyl groups, and the like. For example, the alkyl group is a $C_1$ to $C_8$ alkyl group, including all integer numbers of carbons and ranges of numbers of carbons therebetween. Alkyl groups can be substituted with various other functional groups. For example, the alkyl groups can be substituted with groups such as, for example, amines (acyclic and cyclic), alcohol groups, ether groups, and halogen atoms.

As used herein, the term "cycloalkyl" group refers to a $C_4$-$C_6$ cyclic hydrocarbon group, e.g., cyclopropyl, cyclobutyl, cyclohexyl, and cyclopentyl groups. Cycloalkyl groups can be saturated or partially unsaturated ring systems optionally substituted with, for example, one to three groups, independently selected from the group consisting of alkyl, —$NH_2$, oxo (=O), phenyl, naphthyl, haloalkyl (e.g., —$CF_3$), halo (e.g., —F, —Cl, —Br, —I), alkoxy, and —OH groups. Additionally, alkyl substituents can be substituted with various other functional groups.

As used herein, unless otherwise indicated, "halogen" means fluorine, chlorine, bromine, and iodine, and "halo" group means fluoro, chloro, bromo and iodo.

As used herein, the term "heterocycle" or "heterocyclic" group, unless otherwise stated, refers to a cyclic compound having a ring where at least one or more of the atoms forming the ring is a heteroatom (e.g., oxygen, nitrogen, sulfur, etc.). The heterocyclic ring can be aromatic or nonaromatic, and include compounds that are saturated, partially unsaturated or fully unsaturated. Examples of such groups include azetidine, pyrrolidine, piperdine, azepane, azocane, dihydropyridinone, dihydropyridazinone, dihydrooxepinone, dihydroazepineone, furan, thiophene, oxazole, isoxazole, thiazole, oxadiazole, thiadiazole, triazolo, tetrazole, oxazoline, lactam, lactone, dihydrofuran, tetrahydrofuran, furanone, oxazolone, pyridinone, pyrimidinone, dihydropyridazine, pyranone, oxazinone, and the like. For example, the heterocyclic ring can be a 3, 4, 5, 6, 7, 8, 9, or 10 membered ring containing a number of carbon atoms ranging between 1 and 7 and a number of heteroatoms ranging between 1 and 7. The ring can be bonded to other rings to form ring systems. The heterocyclic ring can be unsubstituted or substituted with various substituents.

As used herein, unless otherwise indicated, "phenyl" group means

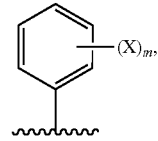

where each X is independently a substituent on the phenyl group and m is from 0 to 5. The substituents at different occurrences can be the same or different. For example, the substituents on the phenyl group include substituted or unsubstituted $C_1$-$C_8$ alkyl, including all integer numbers of carbons and ranges of numbers of carbons therebetween, substituted or unsubstituted amino, haloalkyl (e.g., —$CF_3$), halo (e.g., —F, —Cl, —Br, —I), heterocyclic, substituted or unsubstituted alkoxy (e.g., —OMe), and carbonyl containing moieties such as esters and amides. In certain instances, two adjacent R groups can be connected through to form a dioxolyl group.

As used herein, unless otherwise stated, the term "substituents" or "substituted" refers to one or more of the following groups: alkyl groups, amide groups, amino groups, alkoxy groups, aryl groups, cycloalkyl groups, halogen atoms, alkylhalides, heterocyclic groups, hydroxyl groups, ketone, groups, phenyl groups, or a combination thereof.

The disclosure comprises methods and compounds, where the compounds have one of the following structures:

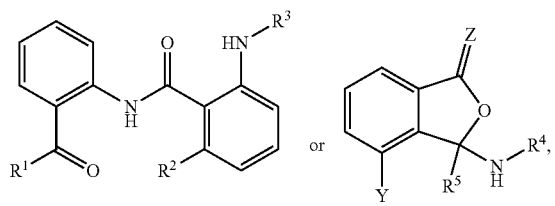

where $R^1$ is selected from the group consisting of —OH, —OMe, and —NHR$^6$, where $R^6$ is selected from the group consisting of $C_1$-$C_5$ alkyl, $C_3$-$C_6$ cycloalkyl, pyridine, and phenyl; $R^2$ is selected from the group consisting of —H, —F, —Cl, —OMe, and —OH; $R^3$ is selected from the group consisting of $C_4$-$C_6$ cycloalklyl, phenyl and pyridine; $R^4$ is selected from the group consisting of $C_1$-$C_8$ alkyl, $C_4$-$C_6$ cycloalklyl, substituted or unsubstituted phenyl, substituted or unsubstituted alkyl amine, substituted or unsubstituted naphthyl and heterocyclic; $R^5$ is selected from the group consisting of

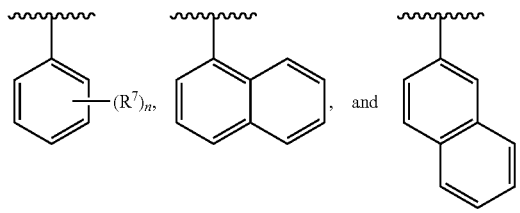

where $R^7$ is independently selected from the group consisting of halogen atom, phenyl, and alkyl; n equals 0-5, Y is —H, —F, —Cl, or -Me; and Z is O or NR$^8$, where $R^8$ is

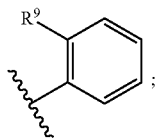

and $R^9$ is selected from the group consisting of —OMe and —F.

In an embodiment, the compound has the following structures:

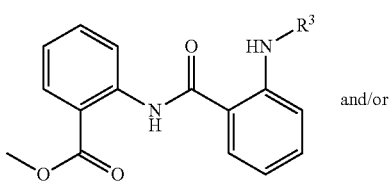

and/or

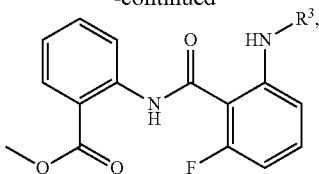

where $R^3$ is selected from the group consisting of $C_4$-$C_6$ cycloalkyl, phenyl, and pyridine.

In an embodiment, the compound has the following structures:

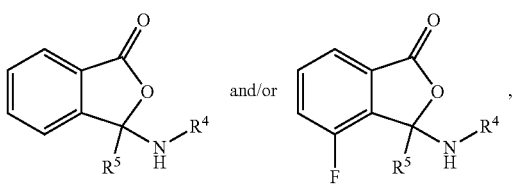

where $R^4$ is selected from the group consisting of $C_1$-$C_8$ alkyl, $C_4$-$C_6$ cycloalklyl, substituted phenyl, substituted or unsubstituted alkyl amine, naphthyl, substituted naphthyl and heterocyclic; and $R^7$ is selected from the group consisting of H, halogen, phenyl, and alkyl.

In an embodiment, the compound has the following structures:

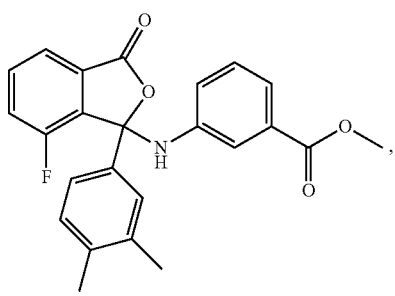

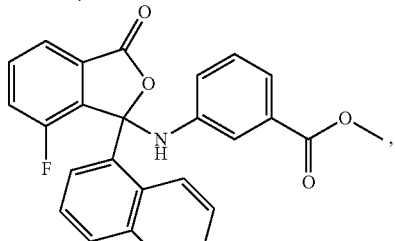

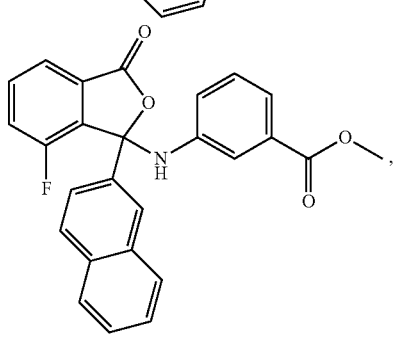

-continued

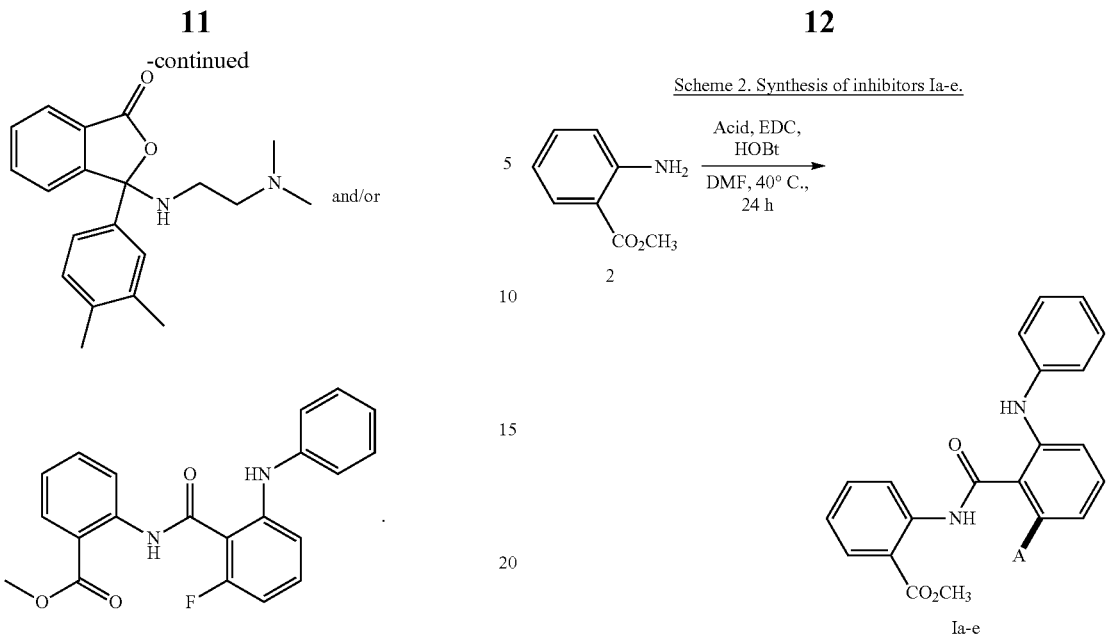

Scheme 2. Synthesis of inhibitors Ia-e.

a, A = H; b, A = F; c, A = Cl; d, A = OMe; e, A = OH

Without intending to be bound by any particular theory, a representative scheme is presented herein to describe the synthesis of the aforementioned molecules:

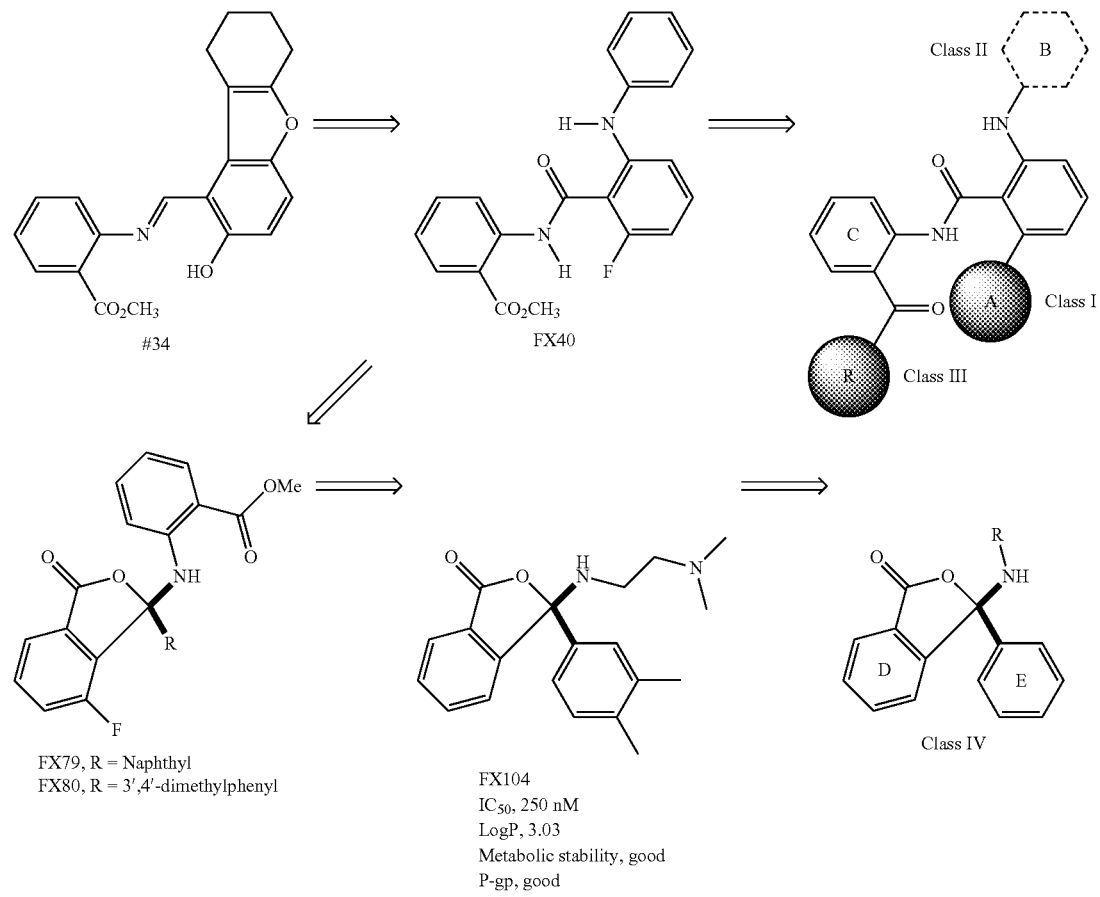

Scheme 1. Design of new LHR-1 antagonists I-IV.

FX79, R = Naphthyl
FX80, R = 3′,4′-dimethylphenyl

FX104
IC$_{50}$, 250 nM
LogP, 3.03
Metabolic stability, good
P-gp, good

Scheme 3. Synthesis of inhibitors IIa-e.

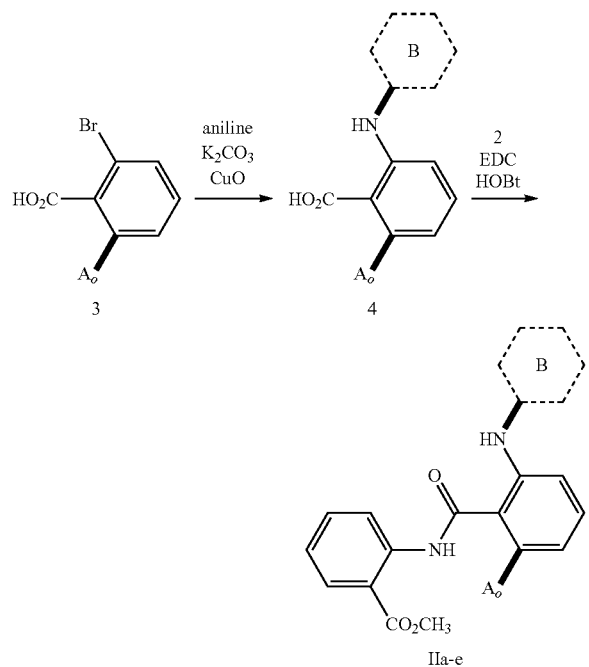

a, B = Ph; b, B = pyridnyl; c, B = cyclohexanyl; d, B = cyclopentanyl; e, B = cyclobutanyl Scheme 4. Synthesis of inhibitors IIIa-p.

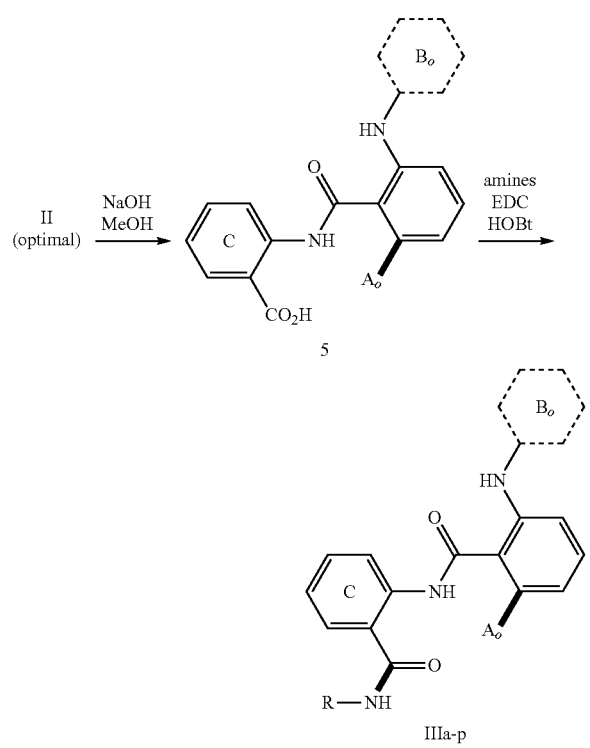

a, R = Et; b, R = n-Pr; c, R = n-Bu; d, R = n-Pen
e, R = i-Pr; f, R = i-Bu; g, R = s-Bu; h, R = i-Pen
i, R = c-Pr; j, R = c-Bu; k, R = c-Pen; l, R = c-Hex
m, R = Ph; n, R = pyrodinyl; o, R = halophenyl; p, R = methoxyphenyl Scheme 5. Synthesis of antagonists IV.

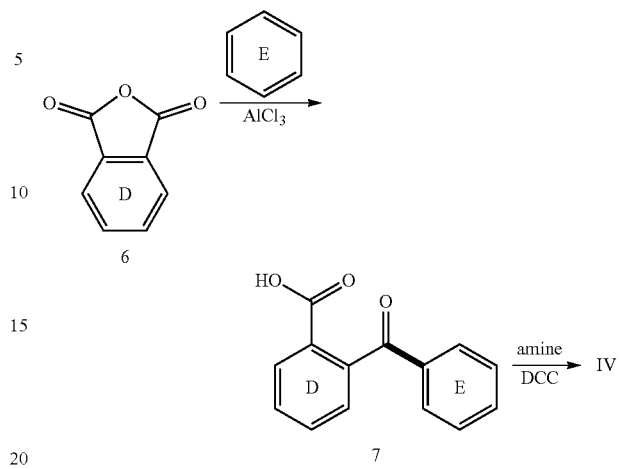

Compounds of this disclosure were designed in part using the following information and approach.

HRG-1 Heme Transporters and Heme Homeostasis: The identification of HRG-1, the first metazoan heme importer/transporter, was accomplished using *C. elegans*, a roundworm that does not synthesize its own heme. HRG-1 and its paralog HRG-4 is a four transmembrane domain permease with homologs in vertebrates. Knockdown of hrg1 in zebrafish causes congenital malformations and profound anemia. In mammals, HRG1 is strongly expressed in macrophages of the reticuloendothelial system and specifically localizes to the phagolysosomal membranes during erythrophagocytosis (EP), a process that degrades over 5 million senescent RBCs per second. Depletion of Hrg1 in mouse macrophages causes attenuation of heme transport from the phagolysosomal compartment confirming that the long-sought heme transporter for macrophage heme-iron recycling is the mammalian homolog of *C. elegans* HRG-1.

Implications for Host-Pathogen Interactions: Like *C. elegans*, kinetoplastid parasites such as *Trypanosomes* and *Leishmania* cannot synthesize heme as they lack most of the heme synthesizing enzymes. The *Leishmania* ortholog of worm HRG-4 is designated LHR1, and was the first parasite heme transporter to be identified. Loss of a single LHR1 allele (LHR1$^{+/-}$) causes severe growth defects while LHR1 null mutants (LHR1$^{-/-}$) are not viable which indicates that LHR1-dependent heme transport is essential for parasite survival and that 50% reduction in LHR1 function is sufficient to significantly impair growth.

A HTS to identify small molecule antagonists of LHR1: To develop a cell-based high throughput screen (HTS) for small molecule antagonists of the LHR1, a heterologous yeast assay was developed. While *S. cerevisiae* synthesize their own heme (like humans), they lack a dedicated plasma membrane heme transporter. Correspondingly, yeast that are genetically defective in heme synthesis (Δhem1 mutant) are unable to grow unless they express LHR1 or HRG1 orthologs in the presence of low amounts of supplemented heme in the growth medium. However, if wildtype yeast expressing LHR1 are grown in the presence of a toxic heme analog gallium protoporphyrin IX (GaPPIX) instead of heme in the growth medium, the yeast die because misincorporation of GaPPIX into the yeast hemoproteins is cytotoxic as gallium cannot undergo redox reactions like the iron within heme. To exploit this assay, yeast stably-transformed with LHR1 were cultured in 384-well plates and candidate small molecule antagonists of LHR1 were identified from a chemical library of >200,000 compounds on the basis of "rescuing" yeast growth in the presence of the toxic GaPPIX as measured by optical absorbance for growth using a plate reader. The small molecule library was composed of the following compounds: 75,000 (ChemBridge Corp.); 100,000 (Chemical Diversity Labs); 22,000 (ComGenex); 1200 (TimTek), 1100 (Prestwick); and 450 (NIH clinical collection). The compounds in the library satisfy a relaxed set of Lipinsky's rules with 99% having a molecular weight<550 Da.

Figure 5:
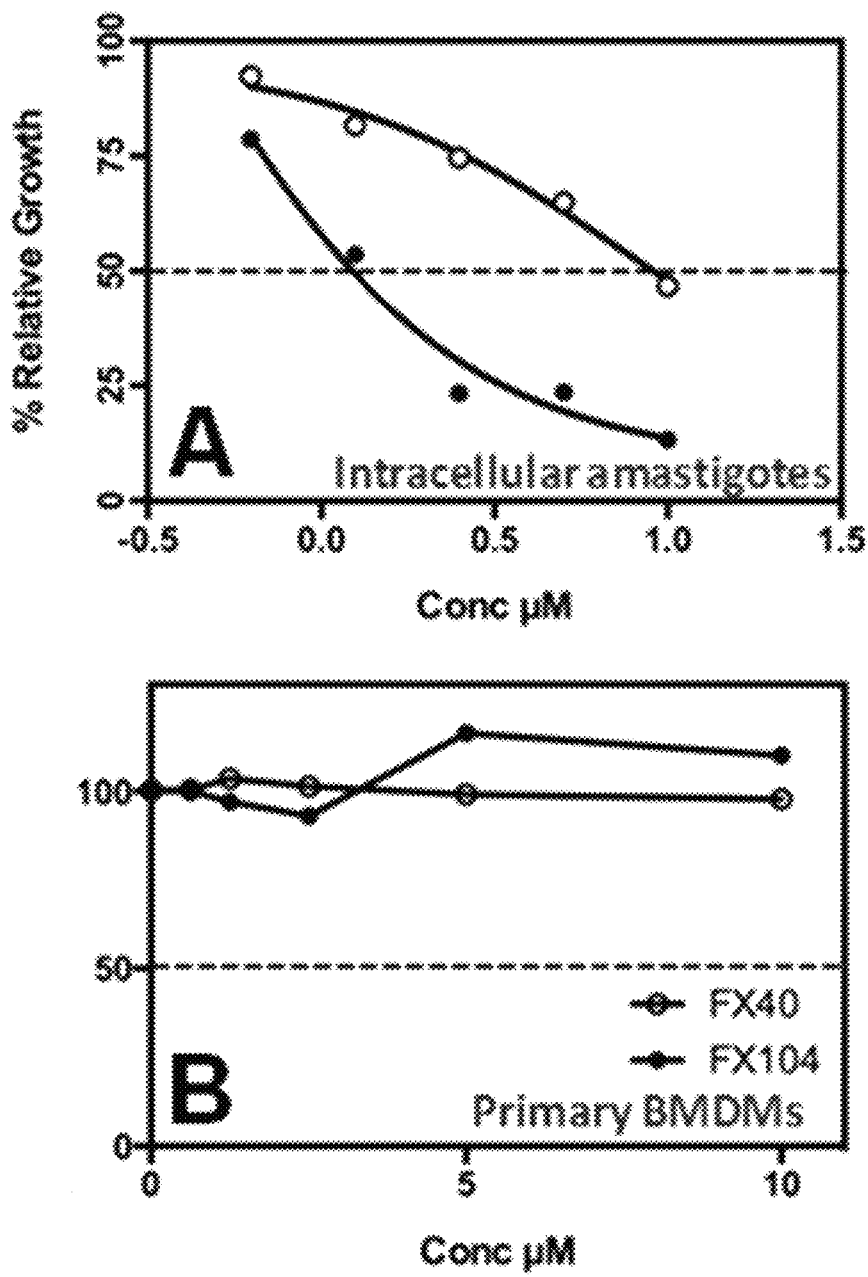
FIG. 5. Dose response curves ($IC_{50}$) of FX40 (○) and the novel derivative compound FX104 (●). (A) BMDMs infected with *L. amazonensis* amastigotes were treated with various concentrations of the indicated compound for 72 h. BMDMs were lysed and released amastigotes were transformed to promastigotes for 48 h at 26° C. $IC_{50}$ values were calculated by quantitation of % promastigote growth using AlamarBlue. (B) Dose response of uninfected BMDMs to compounds. (C) A table showing selectivity criteria for drug efficacy studies. (D) A table showing a summary of high throughput screening.
Figure 5:
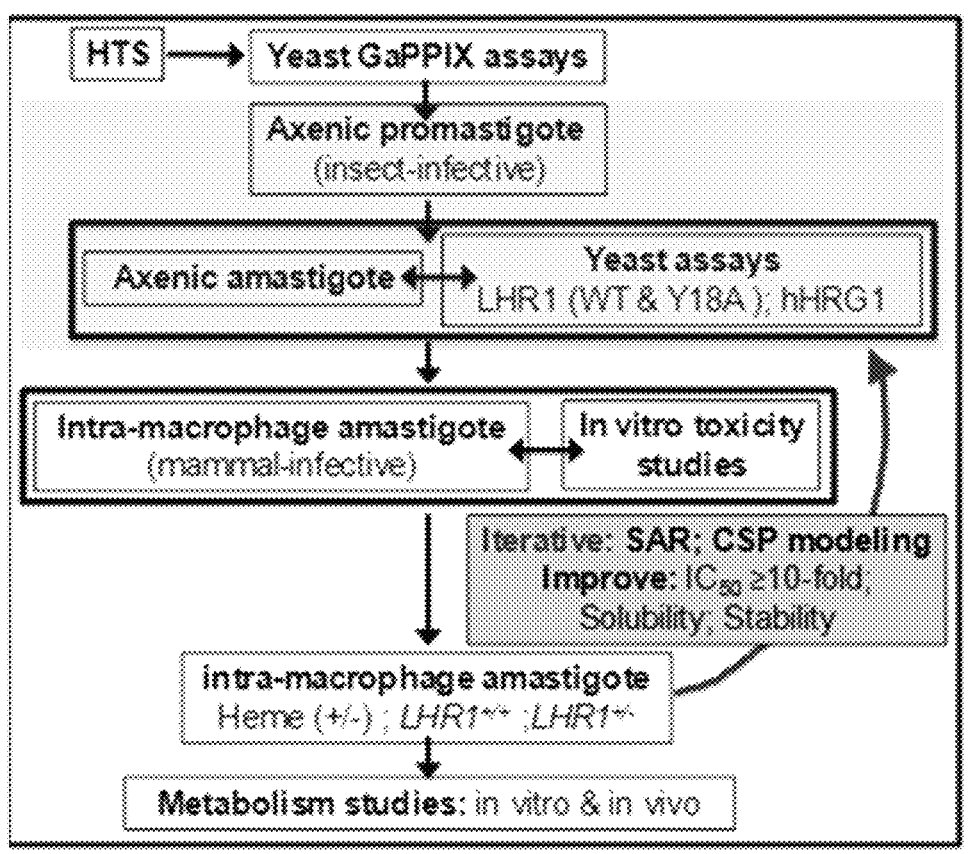
Figure 5:
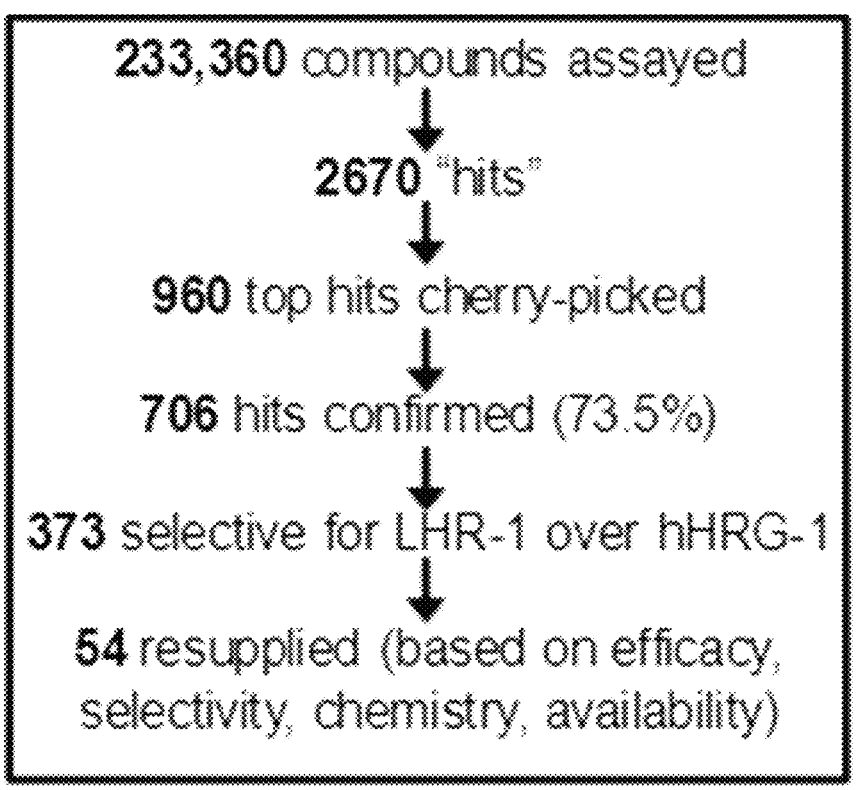

Validation and selectivity of compounds that antagonize LHR1 but not human HRG1: The top 960 hits, defined as being >3 standard deviations from the mean, were "cherry-picked" for validation and preliminary selectivity assessment (FIG. 5D). From these hits, 373 displayed some activity even at 10-fold lower concentration (0.5 µM) with the nine best leads able to fully rescue yeast growth under assay conditions. Though some of these sub-µM leads appeared to inhibit GaPPIX uptake in counterscreens of yeast expressing HRG-1's from other species such as *C. elegans* and human hHRG1, many were selective, displaying little or no human HRG1 antagonism, ruling out the possibility that the hits simply coordinate to GaPPIX. From the 373 compounds that showed selectivity for LHR1 over hHRG1 in the yeast assays, compounds that possessed chemically labile structures, shared similar chemical scaffolds, or showed poor (high) $IC_{50}$ values in dose-response curves in yeast were eliminated. This resulted in the identification of 54 most efficacious compounds, all of which were next tested in *Leishmania* grown in normal medium or in heme depleted medium which upregulates LHR1 (FIG. 1A).

Validation of compounds in *Leishmania*: Several of the initial hits are toxic to *L. amazonensis* promastigotes at 50 M, with enhanced toxicity observed in wildtype strains grown in heme-deficient media that upregulates LHR1, supporting the concept that the drug effects are mediated, in part, through the LHR1 transporter itself (FIG. 1A). Although some of the HTS hits appear to have metabolic and chemical liabilities, several chemical series represent potent and drug-like inhibitors. Strikingly, some of the compounds decreased *L. amazonensis* viability in axenic culture by >90% at 5 µM and 10 µM such as Cmpd #34, a 6,7,8,9-tetrahydro-2-hydroxy-1-dibenzofuranyl derivative. This compound was not identified from any other HTS that is publicly available (FIGS. 1A&B).

Figure 4:
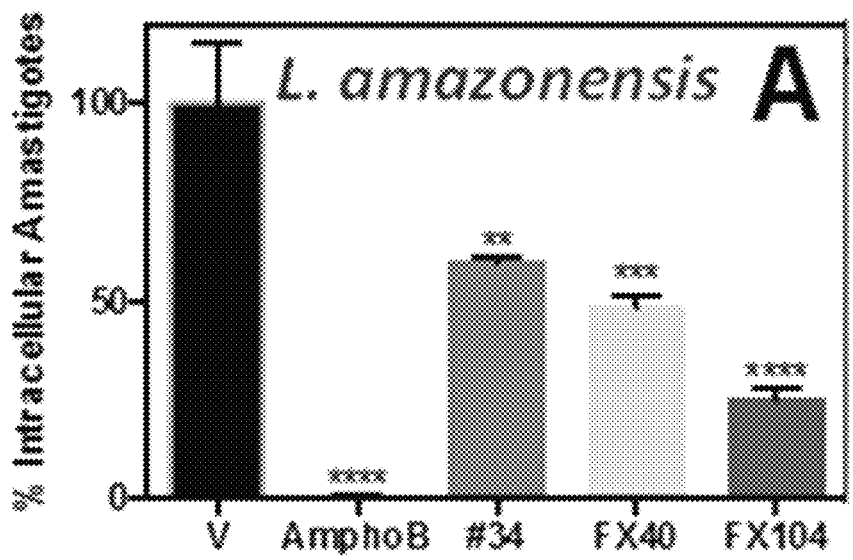
FIG. 4. Inhibition of intra-macrophage *Leishmania* amastigotes. Mouse primary BMDMs were first infected with (A) *L. amazonensis* amastigotes or (B) *L. donovani* metacyclic promastigotes followed by incubation with the indicated compounds at a concentration of 15 μM or DMSO (V), which was used as a negative control, or 0.25 μM amphotericin B (AmphoB), which was used as a positive control. Surviving intracellular amastigotes per 100 macrophages were quantified as determined by DAPI positive cells. **$p<0.0001$, *$p<0.001$, **$p<0.005$.
Figure 4:
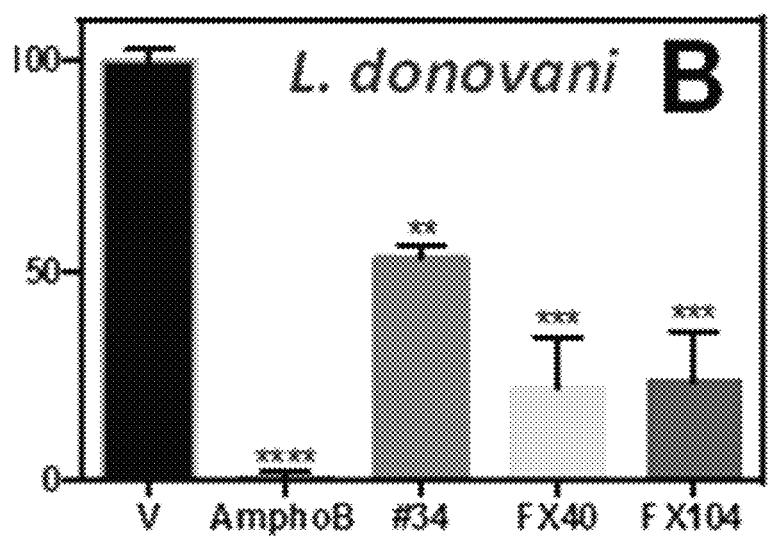

To validate the in vivo efficacy of lead compounds against intracellular amastigotes in macrophages, primary bone marrow-derived macrophages (BMDMs) from mice were obtained and infected them with *L. amazonensis* amastigotes followed by incubation for 72 h with LHR1 antagonists or amphotericin B which kills intracellular *Leishmania*, as a positive control. Cells were then fixed and stained with DAPI which permits visualization of the host macrophage nuclei and parasite nuclei and kinetoplasts. Images collected with fluorescent microscopy were used to determine the ratio between total number of parasites and total number of host cells per treatment. Toxicity to host cells were measured by AlamarBlue viability assays. Both Cmpd #34 and novel antagonist FX40 killed about 50% of intracellular *L. amazonensis* amastigotes (FIG. 4A). The demonstration of this property of FX40 led to the development of FX104. (Sch.1 and FIG. 4A) The structure of FX104 is shown in Scheme 1. Without intending to be constrained by any particular theory or approach, FX104 was determined to have the best drug-like parameters with significantly lower Log P value; better solubility, absorption and metabolic stability; and decreased P-gp efflux. The results show that (a) the novel compound FX104, synthesized from the original scaffold of FX40, is over 30-fold more effective against intracellular forms of *Leishmania* ($IC_{50}$: 8 µM versus 250 nM, FIG. 5A); and (b) FX104 has little or no toxicity in BMDMs even at 40-fold greater concentrations (FIG. 5B).

*L. donovani* metacyclic promastigotes were selectively enriched using a Ficoll density-step gradient. *L. donovani* metacyclic promastigotes were incubated with BMDMs at a macrophage:promastigote ratio of 1:10. After a 24 h incubation at 37° C. in 5% $CO_2$, non-internalized promastigotes were removed by 4 washes and test compounds were added to the cultures and incubated at 37° C. for 72 h. Intracellular parasite viability was evaluated by DAPI staining. Consistent results obtained with *L. amazonensis*, Cmpd #34, FX40 and FX104 killed between 50-70% of intracellular parasites (FIG. 4B). As shown in FIG. 5C, embodiments of the disclosure include iterative SAR and CSP modeling to improve the efficacy of compounds of this disclosure in intra-macrophage assays, which may be performed prior to evaluating them for metabolic stability and ADME properties. In embodiments, compounds that attain an $IC_{50}$ value that matches or surpasses that for Amphotericin B: $IC_{50}$=0.05-0.1 µM against intra-macrophage *L. amazonensis* or 0.02-0.06 µM for intra-macrophage *L. donovani* (>90% efficacy) are provided.

To further assess the chemical stability of compounds of this disclosure, the compounds can be incubated with simulated gastric fluid, simulated intestinal fluid, mouse plasma, mouse liver S9 fraction as well as Caco-2 cell homogenate, and assessed as follows. After incubation for varying times, samples are removed and subsequently ice-cold acetonitrile is added to precipitate cellular protein and stop enzymatic activity. The samples are centrifuged at 12,000×g at 4° C. for 30 min and supernatant are collected for LC-MS/MS analysis. To determine the enzymes responsible for the metabolism of the compounds, mouse or human liver microsomes are prepared by differential centrifugation. The test compounds are incubated with microsomal preparation for varying times, along with representative cytochrome P450 (CYP) inhibitors and antibodies. The metabolic reactions are stopped and the extracted samples are subjected to LC-MS/MS analysis for metabolite identification, quantitation, and metabolism kinetics. For toxicity evaluation in cells, the effect of lead compounds on the viability (MTT assay), cellular morphology (microscopy and histology), and nucleic acid stability (DNA fragmentation) can be evaluated, for example, in HeLa, HepG2, and/or HEK293 cells.

The following materials and methods were employed to synthesize compounds of this disclosure as described in the Examples.

Synthesis Materials and Methods:

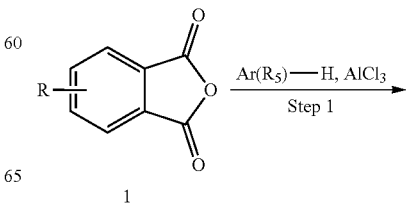

1

-continued

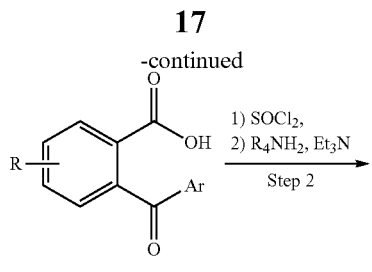

Step 1: To a solution of compound 1 in toluene was added Ar(R5)-H followed by AlCl3. The reaction mixture was allowed to stir for 24 h, and then concentrated. After removing the solvent, the crude material was purified by flash column chromatograph to get compound 2.

Step 2: To a solution of compound 2 in dichloromethane was added SOCl2. The reaction was heated under reflux for 2 h. After removing the solvent, the resulting material was redissolved in DMF, to the resulting solution was added the amino compound R4NH2, followed by triethylamine. The reaction mixture was allowed to stir at room temperature overnight, and then concentrated. After removing the solvent, the crude material was purified by flash column chromatograph to get the final compounds. Examples of compounds encompassed by this disclosure include but are not limited to the following:

Example 1

The following is an example of synthesis and characterization of a compound of the present disclosure. Methyl 2-(4-fluoro-1,3-dihydro-3-(naphthalen-2-yl)-1-oxoisobenzofuran-3-ylamino)benzoate

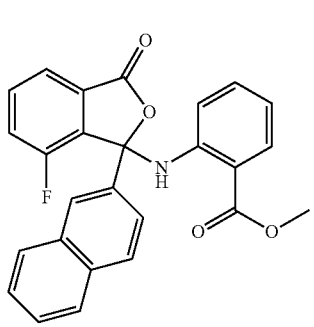

XH3027

$C_{26}H_{18}FNO_4$
Mol. Wt.: 427.4

Yield 31.0%. $^1$H NMR (400 MHz, CDCl$_3$) δ (ppm) 9.51 (s, 1H), 8.12 (s, 1H), 7.96-7.94 (d, J=7.6 Hz, 1H), 7.82-7.77 (m, 4H), 7.71-7.73 (d, J=8.4 Hz, 1H), 7.58-7.52 (m, 1H), 7.48-7.46 (m, 2H), 7.32-7.28 (t, J=8.4 Hz, 1H), 7.08-7.04 (t, J=8.0 Hz, 1H), 6.79-6.76 (d, J=8.4 Hz, 1H), 6.74-6.70 (t, J=8.0 Hz, 1H), 3.90 (s, 3H). $^{13}$C NMR (100 MHz, CDCl$_3$) δ (ppm) 164.3, 163.4, 52.8, 150.3, 141.4, 132.0, 130.0, 129.2, 128.6, 128.4, 128.2, 128.1, 126.6, 124.3, 123.8, 122.8, 122.1, 121.8, 121.0, 118.8, 117.8, 117.6, 117.4, 113.6, 112.5, 108.3, 90.7, 47.3. ESI-MS m/z 426.1 [M−H]$^-$.

Example 2

The following is an example of synthesis and characterization of a compound of the present disclosure. Methyl 2-(4-fluoro-1,3-dihydro-3-(3,4-dimethylphenyl)-1-oxoisobenzofuran-3-ylamino) benzoate

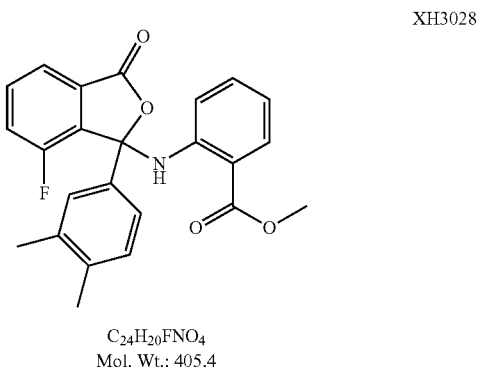 [SMILES: COC(=O)c1ccccc1NC1(c2ccc(C)c(C)c2)OC(=O)c2cccc(F)c21]

XH3028

$C_{24}H_{20}FNO_4$
Mol. Wt.: 405.4

Yield 31.8%. $^1$H NMR (400 MHz, CDCl$_3$) δ (ppm) 9.37 (s, 1H), 7.95-7.93 (d, J=7.2 Hz, 1H), 7.75-7.73 (d, J=7.6 Hz, 1H), 7.56-7.50 (m, 1H), 7.37-7.27 (m, 3H), 7.15-7.11 (t, J=7.6 Hz, 1H), 7.09-7.07 (d, J=7.6 Hz, 1H), 6.75-6.71 (m, 2H), 3.87 (s, 1H), 2.20 (s, 6H). $^{13}$C NMR (100 MHz, CDCl$_3$) δ (ppm) 169.0, 168.4, 155.2, 146.2, 137.9, 137.6, 134.9, 134.0, 132.8, 131.5, 130.5, 128.7, 127.2, 123.9, 122.7, 122.5, 122.2, 118.4, 117.4, 51.9, 19.9, 19.4. ESI-MS m/z 404.1 [M−H]$^-$.

Example 3

The following is an example of synthesis and characterization of a compound of the present disclosure. Methyl 2-(4-fluoro-1,3-dihydro-1-oxo-3-p-tolylisobenzofuran-3-ylamino)benzoate

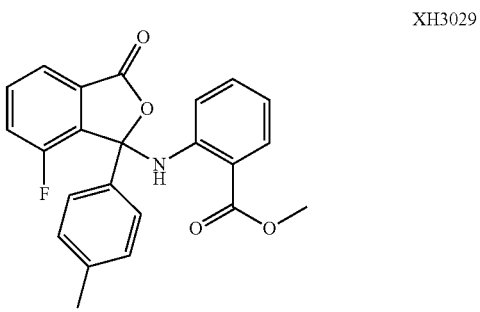

XH3029

$C_{23}H_{18}FNO_4$
Mol. Wt.: 391.4

Yield 32.6%. $^1$H NMR (400 MHz, CDCl$_3$) δ (ppm) 9.40 (s, 1H), 7.97-7.95 (d, J=8.0 Hz, 1H), 7.77-7.75 (d, J=6.8 Hz, 1H), 7.58-7.53 (m, 1H), 7.53-7.50 (d, J=7.6 Hz, 1H), 7.37.34-7.32 (t, J=7.6 Hz, 1H), 7.17-7.13 (m, 3H), 6.75-6.72 (m, 2H), 3.89 (s, 3H), 2.32 (s, 3H). $^{13}$C NMR (100 MHz, CDCl$_3$) δ (ppm) 169.1, 168.2, 157.6, 155.12, 146.3, 139.1, 136.8, 134.4, 133.9, 132.8, 131.4, 129.8, 128.6, 126.2, 122.5, 122.3, 122.1, 118.3, 117.3, 113.1, 95.6, 52.0, 21.2. ESI-MS m/z 390.1 [M−H]⁻.

Example 4

The following is an example of synthesis and characterization of a compound of the present disclosure. 2-(4-fluoro-1,3-dihydro-3-(naphthalen-2-yl)-1-oxoisobenzofuran-3-ylamino)-N-methylbenzamide

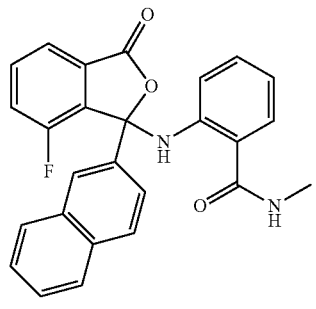

XH3031

$C_{26}H_{19}FN_2O_3$
Mol. Wt.: 426.4

Yield 39.9%. ¹H NMR (400 MHz, CDCl₃) δ (ppm) 9.46 (s, 1H), 8.06 (s, 1H), 7.75-7.67 (m, 5H), 7.48-7.43 (m, 1H), 7.40-7.38 (m, 2H), 7.30-7.28 (d, J=7.6 Hz, 1H), 7.22-7.20 (m, 1H), 6.95-6.91 (t, J=8.0 Hz, 1H), 6.73-6.71 (d, J=8.8 Hz, 1H), 6.66-6.62 (t, J=6.8 Hz, 1H), 6.12 (br s, 1H), 2.92-2.91 (d, 3H). ¹³C NMR (100 MHz, CDCl₃) δ (ppm) 169.0, 168.4, 155.2, 144.2, 135.0, 133.2, 132.6, 132.0, 128.9, 128.6, 127.6, 126.9, 126.4, 123.7, 122.2, 118.4, 29.7, 26.8. ESI-MS m/z 425.1 [M−H]⁻.

Example 5

The following is an example of synthesis and characterization of a compound of the present disclosure. Methyl 2-(1,3-dihydro-1-oxo-3-p-tolylisobenzofuran-3-ylamino)benzoate

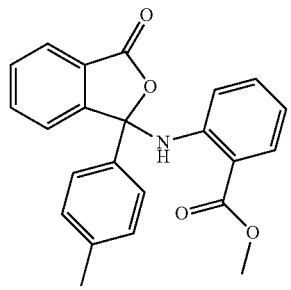

XH3050

$C_{23}H_{19}NO_4$
Mol. Wt.: 373.4

Yield 39.9%. ¹H NMR (CDCl₃) δ (ppm) 9.20 (br s, 1H), 7.96-7.92 (t, J=8.8 Hz, 2H), 7.68-7.64 (t, J=7.6 Hz, 1H), 7.57-7.53 (m, 2H), 7.50-7.48 (d, J=7.6 Hz, 2H), 7.16-7.14 (m, 3H), 6.83-6.81 (d, J=8.8 Hz, 1H), 6.76-6.72 (t, J=7.6 Hz, 1H), 3.87 (s, 3H), 2.30 (s, 3H). ¹³C NMR (CDCl₃) δ (ppm) 169.5, 169.0, 151.5, 146.5, 138.8, 135.9, 135.3, 133.9, 131.2, 130.2, 130.0, 126.0, 125.5, 125.1, 122.1, 118.2, 117.5, 112.9, 91.5, 51.9, 21.1. ESI-MS m/z 372.1 [M−H]⁻.

Example 6

The following is an example of synthesis and characterization of a compound of the present disclosure. Ethyl 3-(1,3-dihydro-1-oxo-3-p-tolylisobenzofuran-3-ylamino)benzoate

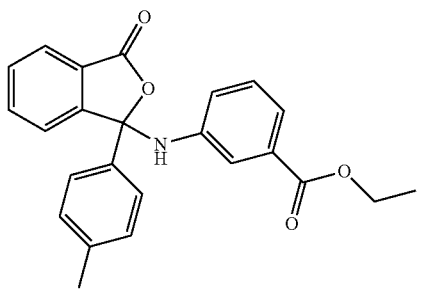

XH3051

$C_{24}H_{21}NO_4$
Mol. Wt.: 387.4

Yield 38.2%. ¹H NMR (400 MHz, CDCl₃) δ (ppm) 7.91-7.89 (d, J=7.6 Hz, 1H), 7.67-7.63 (t, J=7.6 Hz, 1H), 7.57-7.53 (m, 4H), 7.51-7.49 (d, J=7.2 Hz, 1H), 7.38 (s, 1H), 7.18-7.16 (d, J=8.4 Hz, 2H), 7.13-7.09 (t, J=7.6 Hz, 1H), 6.88-6.86 (d, J=8.0 Hz, 1H), 4.29-4.24 (m, 2H), 2.32 (s, 3H), 1.33-1.29 (t, J=7.2 Hz, 3H). ¹³C NMR (100 MHz, CDCl₃) δ (ppm) 169.2, 166.3, 150.7, 142.5, 139.0, 135.8, 134.8, 131.1, 130.3, 129.9, 128.8, 126.0, 125.6, 122.8, 122.4, 122.0, 119.3, 60.8, 21.1, 14.2. ESI-MS m/z 386.1 [M−H]⁻.

Example 7

The following is an example of synthesis and characterization of a compound of the present disclosure. 3-(4-methoxybenzylamino)-3-p-tolylisobenzofuran-1 (3H)-one

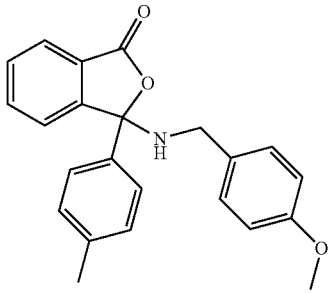

XH3052

$C_{23}H_{21}NO_3$
Mol. Wt.: 359.4

Yield 24.3%. ¹H NMR (400 MHz, CDCl₃) δ (ppm) 7.63-7.62 (d, J=7.6 Hz, 1H), 7.44-7.40 (t, J=7.2 Hz, 1H), 7.38-7.34 (t, J=7.2 Hz, 1H), 7.25-7.20 (m, 2H), 7.07-7.05 (m, 4H), 6.57-6.54 (d, J=8.4 Hz, 2H), 4.49-4.46 (d, J=14.8 Hz, 1H), 4.03-4.00 (d, J 14.8 Hz, 1H), 3.62 (s, 3H), 2.32 (s, 3H). ¹³C NMR (100 MHz, CDCl₃) δ (ppm) 167.9, 158.2, 149.4, 138.0, 135.7, 132.6, 130.3, 130.2, 129.2, 129.0, 126.3, 123.2, 122.6, 113.3, 61.7, 55.1, 42.4, 21.1. ESI-MS m/z 358.2 [M−H]⁻.

Example 8

The following is an example of synthesis and characterization of a compound of the present disclosure. 3-(4-chlorophenylamino)-3-p-tolylisobenzofuran-1 (3H)-one

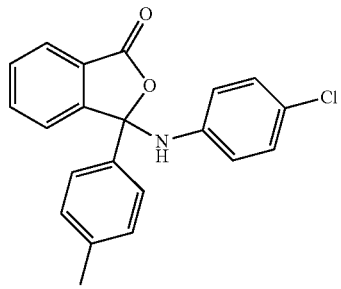

XH3053

$C_{21}H_{16}ClNO_2$
Mol. Wt.: 349.8

Yield 37.4%. ¹H NMR (400 MHz, CDCl₃) δ (ppm) 7.89-7.87 (d, J=8.0 Hz, 1H), 7.65-7.62 (t, J=6.8 Hz, 1H), 7.55-7.52 (m, 2H), 7.17-7.15 (d, J=7.6 Hz, 2H), 7.04-7.01 (d, J=7.6 Hz, 2H), 6.66-6.64 (d, J=8.4 Hz, 2H), 2.32 (s, 3H). ¹³C NMR (100 MHz, CDCl₃) δ (ppm) 169.2, 14.09, 139.2, 135.5, 134.8, 130.4, 129.9, 128.8, 126.1, 125.7, 122.8, 120.0, 21.1. ESI-MS m/z 348.1 [M−H]⁻.

Example 9

The following is an example of synthesis and characterization of a compound of the present disclosure. 3-(pentylamino)-3-p-tolylisobenzofuran-1 (3H)-one

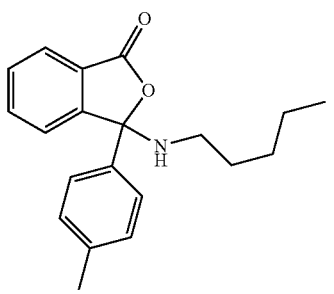

XH3055

$C_{20}H_{23}NO_2$
Mol. Wt.: 309.4

Yield 55.4%. ¹H NMR (400 MHz, CDCl₃) δ (ppm) 7.70-7.68 (d, J=7.2 Hz, 1H), 7.47-7.39 (m, 2H), 7.26-7.25 (m, 3H), 7.14-7.12 (d, J=8.0 Hz, 2H), 3.48 (br s, 1H), 3.44-3.37 (m, 1H), 2.96-2.89 (m, 1H), 2.33 (s, 3H), 1.51-1.45 (m, 1H), 1.38-1.34 (m, 1H), 1.23-1.14 (m, 4H), 0.82-0.78 (t, J=6.8 Hz, 3H). ¹³C NMR (100 MHz, CDCl₃) δ (ppm) 167.7, 149.1, 138.2, 135.6, 132.4, 130.6, 129.4, 129.1, 126.1, 123.1, 122.5, 91.4, 39.6, 29.3, 28.4, 22.2, 21.1, 13.9. ESI-MS m/z 308.2 [M−H]⁻.

Example 10

The following is an example of synthesis and characterization of a compound of the present disclosure. 3-(3,4-dimethylphenyl)-3-(propylamino)isobenzofuran-1 (3H)-one

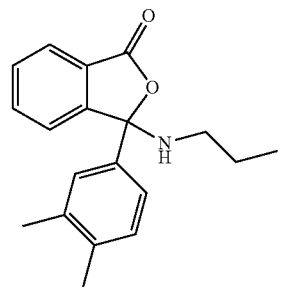

XH3057

$C_{19}H_{21}NO_2$
Mol. Wt.: 295.4

Yield 24.7%. ¹H NMR (400 MHz, CDCl₃) δ (ppm) 7.59-7.57 (d, J=7.2 Hz, 1H), 7.45-7.42 (t, J=8.0 Hz, 1H), 7.38-7.34 (t, J=8.0 Hz, 1H), 7.27-7.25 (d, J=7.2 Hz, 1H), 7.13-7.07 (m, 3H), 4.12 (s, 1H), 3.37-3.30 (m, 1H), 2.90-2.82 (m, 1H), 2.24 (s, 3H), 2.22 (s, 3H), 1.51-1.47 (m, 1H), 1.40-1.34 (m, 1H), 0.79-0.75 (t, J=7.2 Hz, 3H). ¹³C NMR (100 MHz, CDCl₃) δ (ppm) 167.9, 149.3, 136.8, 136.7, 136.0, 132.4, 130.4, 129.7, 129.1, 127.1, 123.6, 123.1, 122.5, 91.5, 41.3, 22.0, 19.9, 19.5. 11.7. ESI-MS m/z 294.1 [M−H]⁻.

Example 11

The following is an example of synthesis and characterization of a compound of the present disclosure. 3-(isopropylamino)-3-(3,4-dimethylphenyl)isobenzofuran-1 (3H)-one

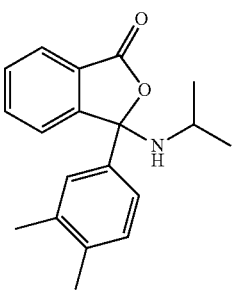

XH3058

$C_{19}H_{21}NO_2$
Mol. Wt.: 295.4

Yield 19.6%. ¹H NMR (400 MHz, CDCl₃) δ (ppm) 7.68-7.66 (m, 1H), 7.41-7.38 (m, 2H), 7.20-7.14 (m, 3H), 7.09-7.07 (d, J=8.0 Hz, 1H), 3.60-3.55 (m, 1H), 3.47 (br s, 1H), 2.24 (s, 3H), 2.22 (s, 3H), 1.42-1.41 (d, J=6.8 Hz, 3H), 1.26-1.24 (d, J=6.8 Hz, 3H). ¹³C NMR (100 MHz, CDCl₃) δ (ppm) 167.4, 148.8, 136.7, 136.5, 136.0, 132.2, 131.6, 130.9, 130.1 & 129.9, 129.7 & 129.5, 129.3, 128.2 & 128.0, 127.7, 123.8, 122.9, 122.4, 91.9, 44.8, 22.3, 21.2, 19.8, 19.5. ESI-MS m/z 318.1 [M+Na]⁺.

Example 12

The following is an example of synthesis and characterization of a compound of the present disclosure. 3-(2-(dimethylamino)ethylamino)-3-(3,4-dimethylphenyl)isobenzofuran-1 (3H)-one

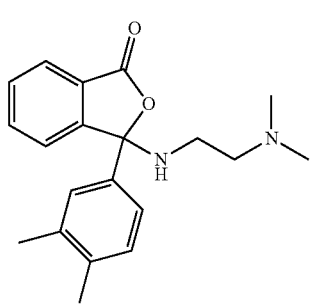

XH3060

$C_{20}H_{24}N_2O_2$
Mol. Wt.: 324.4

Yield 23.6%. $^1$H NMR (400 MHz, CDCl$_3$) δ (ppm) 7.81-7.80 (d, J=6.8 Hz, 1H), 7.44-7.38 (m, 2H), 7.22-7.19 (m, 2H), 7.11-7.09 (m, 2H), 4.14-4.11 (d, J=14.0 Hz, 1H), 2.82-2.73 (m, 2H), 2.28-2.18 (m, 14H). $^{13}$C NMR (100 MHz, CDCl$_3$) δ (ppm) 168.2, 150.1, 137.8, 136.8, 136.6, 132.6, 129.3, 128.6, 127.4, 126.3, 123.9, 123.3, 122.9, 122.2, 58.8, 44.6, 37.0, 19.9, 19.4. ESI-MS m/z 323.2 [M−H]$^-$.

Example 13

The following is an example of synthesis and characterization of a compound of the present disclosure. 3-(3-chlorophenylamino)-3-(3,4-dimethylphenyl)isobenzofuran-1 (3H)-one

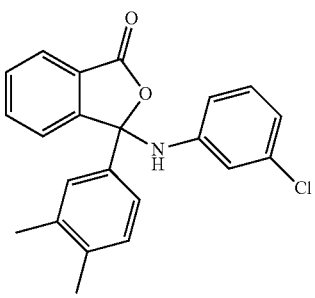

XH3061

$C_{22}H_{18}ClNO_2$
Mol. Wt.: 363.8

Yield 9.70%. $^1$H NMR (400 MHz, CDCl$_3$) δ (ppm) 7.94-7.93 (d, J=6.8 Hz, 1H), 7.69-7.65 (t, J=6.8 Hz, 1H), 7.59-7.54 (m, 2H), 7.42-7.40 (m, 2H), 7.15-7.13 (d, J=7.6 Hz, 1H), 7.02-6.98 (t, J=8.0 Hz, 1H), 6.83-6.82 (d, J=7.6 Hz, 1H), 6.73 (s, 1H), 6.59-6.57 (d, J=7.2 Hz, 1H), 2.25 (s, 6H). $^{13}$C NMR (100 MHz, CDCl$_3$) δ (ppm) 169.2, 143.6, 137.7, 134.8, 134.4, 130.5, 130.4, 129.8, 126.5, 126.1, 123.0, 122.7, 121.0, 118.3, 116.3, 20.0, 19.5. ESI-MS m/z 386.0 [M+Na]$^+$.

Example 14

The following is an example of synthesis and characterization of a compound of the present disclosure. 3-(2-bromophenylamino)-3-(3,4-dimethylphenyl)isobenzofuran-1 (3H)-one

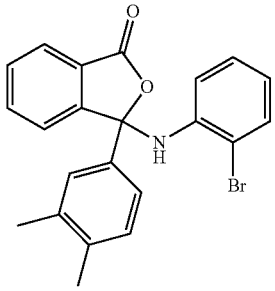

XH3063

$C_{22}H_{18}BrNO_2$
Mol. Wt.: 408.3

Yield 9.70%. $^1$H NMR (400 MHz, CDCl$_3$) δ (ppm) 7.94-7.92 (d, J=6.8 Hz, 1H), 7.68-7.64 (t, J=7.6 Hz, 1H), 7.58-7.54 (m, 2H), 7.46-7.44 (d, J=8.0 Hz, 1H), 7.38-7.36 (m, 2H), 7.12-7.10 (d, J=8.4 Hz, 1H), 6.96-6.93 (t, J=7.2 Hz, 1H), 6.76-6.74 (d, J=6.8 Hz, 1H), 6.70-6.67 (t, J=7.6 Hz, 1H), 2.22 (s, 3H), 2.21 (s, 3H). $^{13}$C NMR (100 MHz, CDCl$_3$) δ (ppm) 169.3, 150.9, 140.0, 137.7, 135.8, 135.0, 132.3, 130.5, 130.4, 127.9, 126.5, 126.1, 125.5, 123.0, 122.5, 121.4, 118.5, 112.4, 20.0, 19.5. ESI-MS m/z 406.1, 408.1 [M−H]$^-$

Example 15

The following is an example of synthesis and characterization of a compound of the present disclosure. 3-(4-bromo-2-methoxyphenylamino)-3-(3,4-dimethylphenyl)isobenzofuran-1 (3H)-one

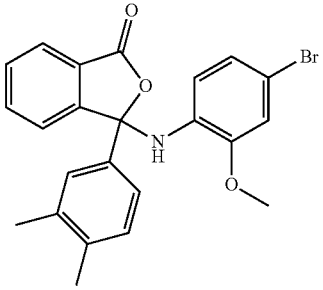

XH3064

$C_{23}H_{20}BrNO_3$
Mol. Wt.: 438.3

Yield 11.1%. $^1$H NMR (400 MHz, CDCl$_3$) δ (ppm) 7.92-7.90 (d, J=8.0 Hz, 1H), 7.66-7.63 (t, J=8.0 Hz, 1H), 7.57-7.53 (m, 2H), 7.39-7.37 (m, 2H), 7.13-7.11 (d, J=8.4 Hz, 1H), 6.90-6.89 (d, J=2.4 Hz, 1H), 6.73-6.70 (dd, J1=8.8 Hz, J2=1.6 Hz, 1H), 6.37-6.34 (d, J=8.8 Hz, 1H), 3.83 (s, 3H), 2.23 (s, 6H). $^{13}$C NMR (100 MHz, CDCl$_3$) δ (ppm) 169.4, 151.0, 148.6, 137.7, 136.2, 134.8, 131.4, 130.5, 130.2, 126.5, 126.0, 125.6, 124.0, 123.8, 123.4, 123.0, 122.7, 117.5, 113.3, 112.0, 55.8, 20.0, 19.5. ESI-MS m/z 460.0, 462.0 [M+Na]⁺.

Example 16

The following is an example of synthesis and characterization of a compound of the present disclosure. 3-(benzylamino)-3-(3,4-dimethylphenyl)isobenzofuran-1 (3H)-one

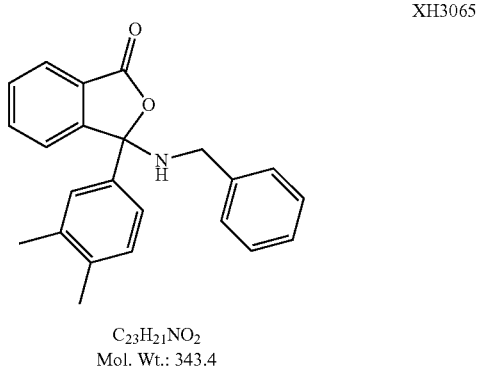 [SMILES: Cc1ccc(C2(NCc3ccccc3)OC(=O)c3ccccc32)cc1C]

XH3065

$C_{23}H_{21}NO_2$
Mol. Wt.: 343.4

Yield 20.6%. ¹H NMR (400 MHz, CDCl₃) δ (ppm) 7.71-7.69 (d, J=3.6 Hz, 1H), 7.44-7.36 (m, 2H), 7.25-7.23 (m, 1H), 7.15-7.08 (m, 5H), 7.03-7.01 (d, J=8.4 Hz, 1H), 6.91 (s, 1H), 4.59-4.56 (d, J=15.6 Hz, 1H), 4.08-4.04 (d, J=15.6 Hz, 1H), 2.19 (s, 3H), 2.09 (s, 3H). ¹³C NMR (100 MHz, CDCl₃) δ (ppm) 168.0, 149.2, 138.1, 136.8, 136.6, 135.5, 132.7, 130.1, 129.6, 129.3, 128.8, 128.0, 127.5, 126.9, 123.7, 123.3, 122.7, 91.7, 43.0, 19.8, 19.4. ESI-MS m/z 342.2 [M−H]⁻.

Example 17

The following is an example of synthesis and characterization of a compound of the present disclosure. Methyl 2-(1,3-dihydro-1-(3,4-dimethylphenyl)-3-oxoisobenzofuran-1-ylamino)benzoate

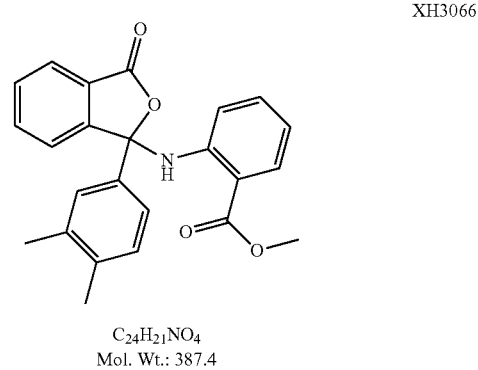 [SMILES: COC(=O)c1ccccc1NC1(c2ccc(C)c(C)c2)OC(=O)c2ccccc21]

XH3066

$C_{24}H_{21}NO_4$
Mol. Wt.: 387.4

Yield 12.8%. ¹H NMR (400 MHz, CDCl₃) δ (ppm) 9.16 (br s, 1H), 8.00-7.91 (t, J=8.0 Hz, 2H), 7.68-7.64 (t, J=7.6 Hz, 1H), 7.57-7.53 (m, 2H), 7.34-7.33 (m, 2H), 7.18-7.16 (m, 1H), 7.10-7.08 (d, J=8.8 Hz, 1H), 6.83-6.81 (d, J=8.8 Hz, 1H), 6.75-6.72 (t, J=7.6 Hz, 1H), 3.87 (s, 3H), 2.21 (s, 6H). ¹³C NMR (100 MHz, CDCl₃) δ (ppm) 169.6, 169.0, 151.7, 146.6, 137.7, 137.4, 136.2, 135.2, 133.9, 131.2, 130.5, 130.2, 126.5, 126.0, 125.1, 122.9, 122.1, 118.1, 117.5, 112.8, 91.7, 51.9, 20.0, 19.4. ESI-MS m/z 388.1 [M+H]⁺.

Example 18

The following is an example of synthesis and characterization of a compound of the present disclosure. Methyl-2-(4-chloro-1,3-dihydro-3-(3,4-dimethylphenyl)-1-oxoisobenzofuran-3-ylamino) benzoate

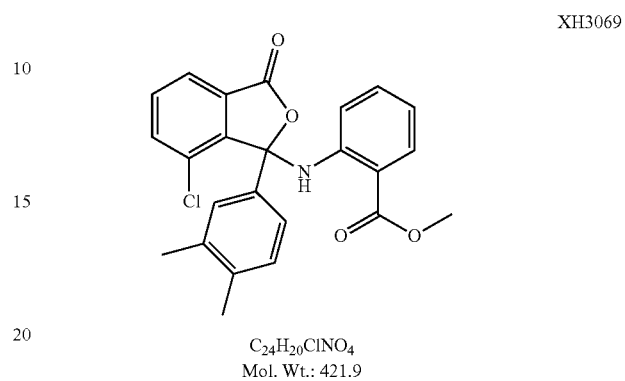

XH3069

$C_{24}H_{20}ClNO_4$
Mol. Wt.: 421.9

Yield 17.9%. ¹H NMR (400 MHz, CDCl₃) δ (ppm) 9.44 (br s, 1H), 7.98-7.96 (d, J=7.2 Hz, 1H), 7.91-7.89 (d, J=7.6 Hz, 1H), 7.60-7.58 (d, J=7.2 Hz, 1H), 7.54-7.51 (t, J=8.0 Hz, 1H), 7.34-7.32 (d, J=7.6 Hz, 1H), 7.24 (s, 1H), 7.16-7.12 (t, J=8.0 Hz, 1H), 7.10-7.08 (d, J=8.8 Hz, 1H), 6.77-6.73 (t, J=8.0 Hz, 1H), 6.70-6.68 (d, J=8.4 Hz, 1H), 3.89 (s, 3H), 2.23 (s, 3H), 2.20 (s, 3H). ¹³C NMR (100 MHz, CDCl₃) δ (ppm) 169.0, 168.2, 146.6, 146.3, 137.8, 137.1, 136.3, 133.8, 132.9, 131.8, 131.3, 129.7, 129.3, 128.7, 127.9, 125.0, 124.6, 118.1, 117.2, 112.9, 91.9, 51.9, 20.0, 19.5. ESI-MS m/z 422.0 [M+H]⁺.

Example 19

The following is an example of synthesis and characterization of a compound of the present disclosure. 3-(2-methoxyphenylamino)-4-chloro-3-p-tolylisobenzofuran-1 (3H)-one

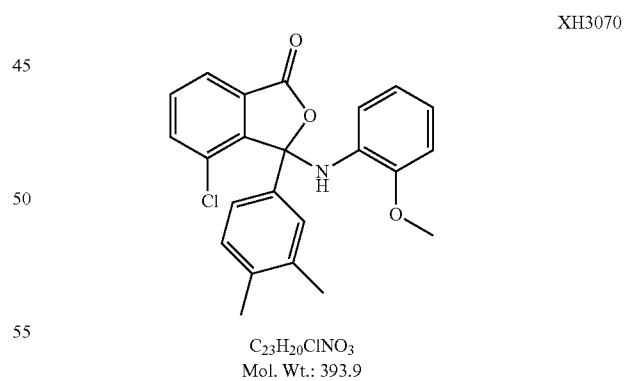

XH3070

$C_{23}H_{20}ClNO_3$
Mol. Wt.: 393.9

Yield 19.7%. ¹H NMR (400 MHz, CDCl₃) δ (ppm) 7.89-7.87 (d, J=7.2 Hz, 1H), 7.58-7.50 (m, 2H), 7.39-7.37 (d, J=7.6 Hz, 1H), 7.34 (s, 1H), 7.13-7.11 (d, J=8.0 Hz, 1H), 6.84-6.76 (m, 2H), 6.61-6.57 (t, J=8.0 Hz, 1H), 6.39-6.37 (d, J=7.6 Hz, 1H), 3.87 (s, 3H), 2.25 (s, 3H), 2.24 (s, 3H). ¹³C NMR (100 MHz, CDCl₃) δ (ppm) 168.1, 148.2, 146.1, 137.9, 137.0, 135.8, 134.0, 131.9, 131.7, 129.7, 129.5, 127.9, 124.7, 124.5, 120.6, 120.2, 116.2, 110.1, 55.7, 20.0, 19.5. ESI-MS m/z 394.1 [M+H]⁺.

Example 20

The following is an example of synthesis and characterization of a compound of the present disclosure. 3-(2-fluorophenylamino)-4-chloro-3-(3,4-dimethylphenyl) isobenzofuran-1 (3H)-one

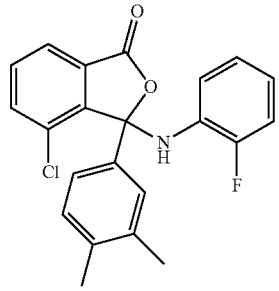

XH3071

C$_{22}$H$_{17}$ClFNO$_2$
Mol. Wt.: 381.8

Yield 29.8%. $^1$H NMR (400 MHz, CDCl$_3$) δ (ppm) 7.90-7.88 (d, J=7.6 Hz, 1H), 7.59-7.51 (m, 2H), 7.38-7.34 (m, 2H), 7.14-7.12 (d, J=8.0 Hz, 1H), 7.05-6.99 (m, 1H), 6.79-6.75 (m, 2H), 6.55-6.51 (m, 1H), 2.25 (s, 3H), 2.24 (s, 3H). $^{13}$C NMR (100 MHz, CDCl$_3$) δ (ppm) 167.8, 154.1, 151.7, 145.5, 138.2, 137.2, 136.0, 133.3, 132.0, 130.7 & 130.6, 129.8, 129.3, 124.6 & 124.6 (1C), 124.0 & 124.0 (1C), 121.0 & 120.9 (1C), 115.0, 114.8, 20.0, 19.5. ESI-MS m/z 382.0 [M+H]$^+$.

Example 21

The following is an example of synthesis and characterization of a compound of the present disclosure. 3-(4-(4-chlorophenoxy)phenylamino)-4-chloro-3-(3,4-dimethylphenyl)isobenzofuran-1 (3H)-one

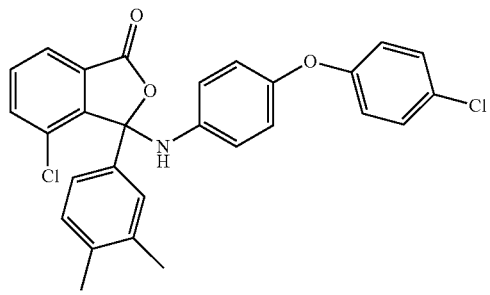

XH3072

C$_{28}$H$_{21}$Cl$_2$NO$_3$
Mol. Wt.: 490.4

Yield 18.2%. $^1$H NMR (400 MHz, CDCl$_3$) δ (ppm) 7.77-7.75 (d, J=6.8 Hz, 1H), 7.51-7.44 (m, 2H), 7.28-7.2 (m, 3H), 7.19-7.16 (d, J=8.8 Hz, 2H), 7.04-6.99 (m, 3H), 6.92-6.89 (d, J=8.8 Hz, 2H), 6.85-6.82 (d, J=8.4 Hz, 2H), 2.20 (s, 3H), 2.15 (s, 3H). $^{13}$C NMR (100 MHz, CDCl$_3$) δ (ppm) 165.9, 155.8, 144.0, 137.1, 136.4, 134.2, 133.9, 133.0, 131.3, 130.1, 129.7, 129.4, 128.8, 127.5, 123.9, 122.3, 120.4, 118.6, 19.9, 19.5. ESI-MS m/z 513.0 [M+Na]$^+$.

Example 22

The following is an example of synthesis and characterization of a compound of the present disclosure. 3,4-bis(2-methoxyphenylamino)-3-p-tolylisobenzofuran-1 (3H)-one

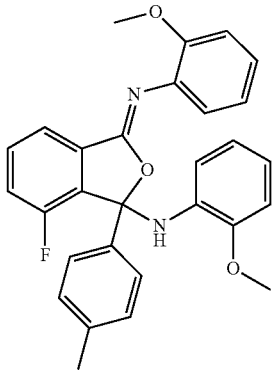

XH3074-1

Chemical Formula: C$_{29}$H$_{25}$FN$_2$O$_3$
Molecular Weight: 468.53

Yield 10.7%. $^1$H NMR (Acetone-d6) δ (ppm) 7.79-7.77 (d, J=7.2 Hz, 1H), 7.70-7.67 (m, 1H), 7.33-7.29 (t, J=8.4 Hz, 2H), 7.10-7.00 (m, 5H), 6.92-6.84 (m, 3H), 6.72-6.69 (t, J=8.0 Hz, 1H), 6.60-6.56 (t, J=8.0 Hz, 1H), 6.40-6.38 (d, J=8.0 Hz, 1H). 5.62 (br s, 1H), 3.85 (s, 3H), 3.17 (s, 3H), 2.29 (s, 3H). $^{13}$C NMR (100 MHz, CDCl$_3$) δ (ppm) 165.3, 158.3, 156.3, 155.8, 148.0, 138.6, 136.3, 135.9, 134.1, 132.2, 131.6 & 131.5, 130.6, 129.7, 128.7, 125.6, 123.1, 121.0, 120.4, 120.0, 119.7, 119.5, 119.0, 113.8, 111.7, 109.8, 81.9, 55.8, 55.2, 21.0. ESI-MS m/z 491.1 [M+Na]$^+$.

Example 23

The following is an example of synthesis and characterization of a compound of the present disclosure. 3-(2-methoxyphenylamino)-4-fluoro-3-p-tolylisobenzofuran-1 (3H)-one

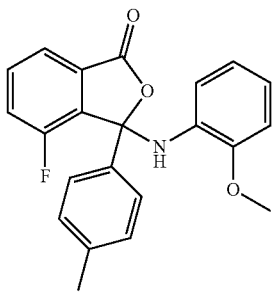

XH3074-2

C$_{22}$H$_{18}$FNO$_3$
Mol. Wt.: 363.4

Yield 31.5%. $^1$H NMR (400 MHz, CDCl$_3$) δ (ppm) 7.76-7.74 (d, J=7.6 Hz, 1H), 7.57-7.53 (m, 1H), 7.32-7.28 (m, 1H), 7.25-7.20 (m, 3H), 7.09-7.07 (d, J=8.0 Hz, 1H), 7.00-6.98 (d, J=8.0 Hz, 1H), 6.85-6.81 (t, J=7.6 Hz, 1H), 6.71-6.69 (d, J=7.6 Hz, 1H), 3.79 (s, 3H), 2.31 (s, 3H). $^{13}$C NMR (100 MHz, CDCl$_3$) δ (ppm) 158.3, 156.0, 155.7, 131.9

& 131.9, 131.5, 130.1, 129.5 & 129.4, 18.8, 126.0, 121.3, 120.5, 120.3, 119.8 & 119.8, 56.1, 21.2. ESI-MS m/z 386.0 [M+Na]+.

Example 24

The following is an example of synthesis and characterization of a compound of the present disclosure. 3,4-bis(2-fluorophenylamino)-3-p-tolylisobenzofuran-1 (3H)-one

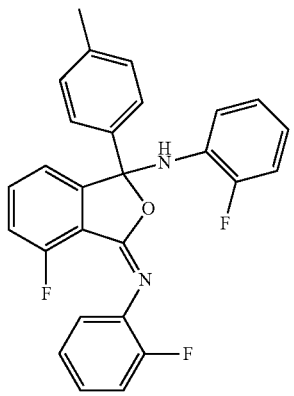

XH3075

Chemical Formula: $C_{27}H_{19}F_3N_2O$
Molecular Weight: 444.46

Yield 14.1%. $^1$H NMR (400 MHz, CDCl$_3$) δ (ppm) 7.93-7.91 (d, J=7.6 Hz, 1H), 7.62-7.58 (m, 1H), 7.36-7.31 (m, 1H), 7.24-7.20 (m, 2H), 7.17-7.10 (m, 5H), 7.08-7.03 (m, 2H), 6.80-6.76 (m, 2H), 6.60-6.54 (m, 1H), 5.25-5.24 (d, J=4.8 Hz, 1H), 2.36 (s, 3H). $^{13}$C NMR (100 MHz, CDCl$_3$) δ (ppm) 165.1, 160.3, 158.2, 157.8, 155.6, 153.8, 151.4, 139.4, 135.4, 134.7, 132.3, 132.1, 132.1, 130.1, 130.0 & 130.0, 129.5, 125.1, 124.5 & 124.5, 124.3 & 124.3, 122.2 & 122.1, 120.3, 120.1 & 120.1, 116.5 & 116.3, 115.8, 114.8 & 114.7, 81.9, 21.1. ESI-MS m/z 467.1 [M+Na]+.

Example 25

The following is an example of synthesis and characterization of a compound of the present disclosure. 3-((pyridin-2-yl)methylamino)-4-fluoro-3-p-tolylisobenzofuran-1 (3H)-one

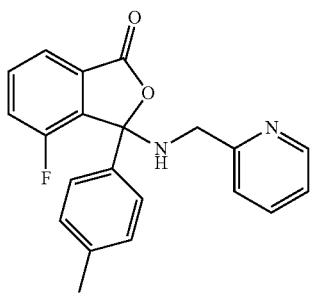

XH3076

$C_{21}H_{17}FN_2O_2$
Mol. Wt.: 348.4

Yield 82.9%. $^1$H NMR (400 MHz, CDCl$_3$) δ (ppm) 9.20 (br s, 1H), 8.41-8.39 (d, J=4.4 Hz, 1H), 7.69-7.65 (td, J1=8.0 Hz, J2=1.6 Hz, 1H), 7.59-7.57 (d, J=7.6 Hz, 1H), 7.42-7.38 (m, 4H), 7.21-7.11 (m, 4H), 5.01-4.97 (d, J=16.4 Hz, 1H), 4.16-4.12 (d, J=16.4 Hz, 1H), 2.32 (s, 3H). $^{13}$C NMR (100 MHz, CDCl$_3$) δ (ppm) 166.9, 158.2, 156.1, 155.7, 148.0, 138.4, 138.0, 136 . . . 2, 132.6, 131.3 & 131.2, 129.3, 126.3, 122.8 & 122.8, 120.3, 120.1, 119.2, 89.5, 44.6, 21.1. ESI-MS m/z 371.1 [M+Na]+.

Example 26

The following is an example of synthesis and characterization of a compound of the present disclosure. 4-fluoro-3-(3,4-dimethylphenyl)-3-(pyridin-2-ylamino)isobenzofuran-1 (3H)-one

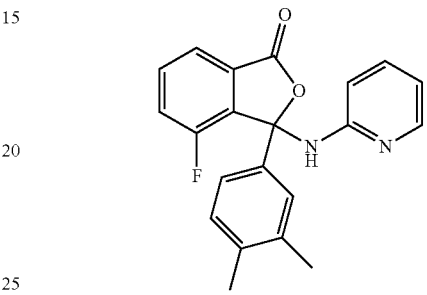

XH3079

$C_{21}H_{17}FN_2O_2$
Mol. Wt.: 348.4

Yield 5.52%. $^1$H NMR (400 MHz, CDCl$_3$) δ (ppm) 8.42-8.40 (d, J=7.6 Hz, 1H), 8.15-8.14 (d, J=4.0 Hz, 1H), 7.78-7.75 (m, 2H), 7.50-7.45 (m, 1H), 7.28-7.24 (m, 2H), 7.21-7.17 (t, J=8.4 Hz, 1H), 7.02-6.98 (m, 2H), 2.16 (s, 6H). $^{13}$C NMR (100 MHz, CDCl$_3$) δ (ppm) 165.9, 158.0 & 155.5 (1C), 151.4, 146.5, 138.6, 137.5, 136.6 & 136.6 (1C), 136.6 & 131.6 (1C), 129.6, 126.9, 123.2, 121.2 &121.1 (1C), 120.0, 120.0, 116.5, 93.2, 19.9, 19.4. ESI-MS m/z 371.0 [M+Na]+.

Example 27

The following is an example of synthesis and characterization of a compound of the present disclosure. 3,4-bis(2-fluorophenylamino)-3-(3,4-dimethylphenyl)isobenzofuran-1 (3H)-one

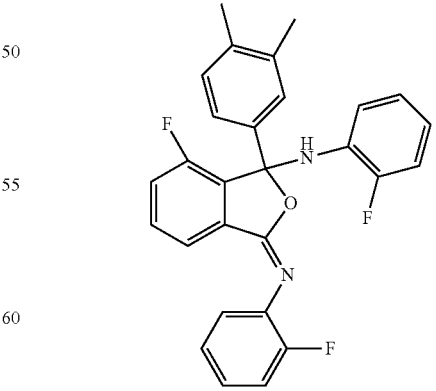

XH3080

Chemical Formula: $C_{28}H_{21}F_3N_2O$
Molecular Weight: 458.48

Yield 31.0%. ¹H NMR (400 MHz, CDCl₃) δ (ppm) 7.88-7.86 (d, J=7.2 Hz, 1H), 7.57-7.52 (m, 1H), 7.30-7.26 (m, 1H), 7.18-7.14 (m, 2H), 7.10-6.97 (m, 6H), 6.76-6.70 (m, 2H), 6.51-6.47 (m, 1H), 5.21-5.20 (d, J=4.8 Hz, 1H), 2.22 (s, 3H), 2.14 (s, 3H). ¹³C NMR (100 MHz, CDCl₃) δ (ppm) 165.1, 160.3, 158.1, 157.8, 155.6, 153.8, 151.4, 138.0, 137.2, 135.7, 134.6, 132.2, 132.0, 130.0, 129.9, 129.8, 126.4, 124.5, 124.2, 122.6, 120.3, 120.1, 120.0, 116.5, 116.3, 115.8, 114.8, 114.6, 81.9, 19.9, 19.5.

Example 28

The following is an example of synthesis and characterization of a compound of the present disclosure. 3-((pyridin-3-yl)methylamino)-4-fluoro-3-(3,4-dimethylphenyl)isobenzofuran-1 (3H)-one

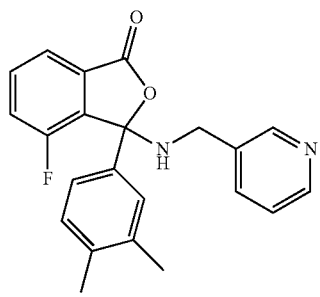

XH3084

C₂₂H₁₉FN₂O₂
Mol. Wt.: 362.4

Yield 68.8%. ¹H NMR (400 MHz, CDCl₃) δ (ppm) 8.19 (br s, 1H), 7.53-7.51 (d, J=6.8 Hz, 2H), 7.45-7.38 (m, 2H), 7.22-7.20 (d, J=7.6 Hz, 1H), 7.15 (s, 1H), 7.13-7.09 (t, J=7.6 Hz, 2H), 6.94-6.91 (m, 1H), 4.64-4.60 (d, J=15.6 Hz, 1H), 4.04-4.00 (d, J=15.6 Hz, 1H), 2.24 (s, 3H), 2.19 (s, 3H). ¹³C NMR (100 MHz, CDCl₃) δ (ppm) 166.6, 158.2 & 155.6 (1C, C—F), 148.2, 146.0, 137.6, 137.2, 135.3 & 135.2 (1C), 135.1, 134.2, 133.2, 131.6 & 131.5 (1C), 129.8, 127.3, 123.8, 123.2, 120.3 & 120.1 (1C), 119.1, 90.6, 40.6, 19.9, 19.5. ESI-MS m/z 363.1 [M+H]⁺.

Example 29

The following is an example of synthesis and characterization of a compound of the present disclosure. 3-(2-methoxyethylamino)-4-fluoro-3-(3,4-dimethylphenyl)isobenzofuran-1 (3H)-one

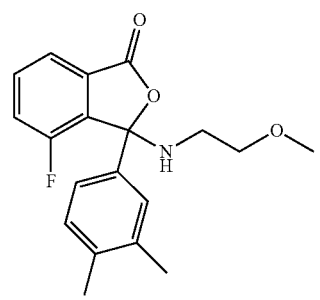

XH3087

C₁₉H₂₀FNO₃
Mol. Wt.: 329.4

Yield 61.4%. ¹H NMR (400 MHz, CDCl₃) δ (ppm) 7.64-7.62 (d, J=7.2 Hz, 1H), 7.45-7.40 (m, 1H), 7.16-7.09 (m, 4H), 6.07 (br s, 1H), 4.02-3.99 (d, J=14.0 Hz, 1H), 3.67-3.62 (t d, J1=10.0 Hz, J2=1.6 Hz, 1H), 3.38 (s, 3H), 3.01-2.93 (m, 1H), 2.23 (s, 3H), 2.22 (s, 3H). ¹³C NMR (100 MHz, CDCl₃) δ (ppm) 166.9, 158.1, 155.6, 137.1 & 136.9 (1C), 135.7, 134.9 & 134.8 (1C), 132.8, 131.4 & 131.3 (1C), 129.9, 127.2, 123.8, 120.2 & 120.0 (1C), 119.2 & 119.2 (1C), 89.4, 70.9, 58.9, 39.3, 19.9, 19.5. ESI-MS m/z 352.1 [M+Na]⁺.

Example 30

The following is an example of synthesis and characterization of a compound of the present disclosure. 3-(2-methoxyphenylamino)-4-fluoro-3-(3,4-dimethylphenyl)isobenzofuran-1 (3H)-one

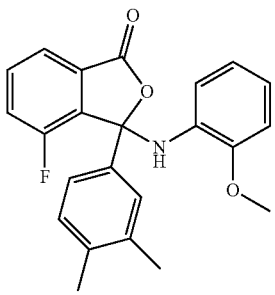

XH3088

C₂₃H₂₀FNO₃
Mol. Wt.: 377.4

Yield 98.8%. ¹H NMR (400 MHz, DMSO-d6) δ (ppm) 7.68-7.62 (m, 2H), 7.51 (br s, 1H), 7.43-7.39 (m, 1H), 7.27-7.23 (t, J=7.6 Hz, 1H), 7.07-7.04 (m, 2H), 6.97-6.93 (t, J=7.6 Hz, 2H), 6.90-6.86 (t, J=7.2 Hz, 1H), 3.49 (s, 3H), 2.13 (s, 3H), 2.09 (s, 3H). ¹³C NMR (100 MHz, DMSO-d6) δ (ppm) 164.7, 158.1, 156.2, 155.6136.3, 136.1, 135.5, 133.9, 132.5, 130.4, 129.6, 129.0, 127.5, 124.1, 120.6, 120.4, 120.2, 119.5, 112.6, 90.9, 55.8, 19.9, 19.5. ESI-MS m/z 400.1 [M+Na]⁺.

Example 31

The following is an example of synthesis and characterization of a compound of the present disclosure. Methyl 2-(1,3-dihydro-1-(4-methoxyphenyl)-3-oxoisobenzofuran-1-ylamino)benzoate

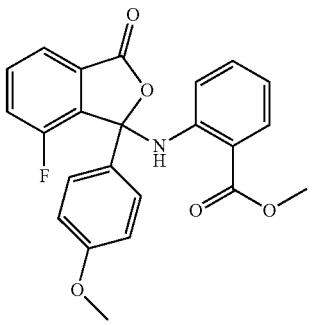

XH3090

C₂₃H₁₉NO₅
Mol. Wt.: 389.4

Yield 43.9%. $^1$H NMR (400 MHz, CDCl$_3$) δ (ppm) 9.15 (br s, 1H), 7.93-7.89 (t, J=8.4 Hz, 2H), 7.66-7.62 (t, J=7.2 Hz, 1H), 7.53-7.47 (m, 4H), 7.15-7.11 (t, J=8.0 Hz, 1H), 6.84-6.79 (m, 3H), 6.73-6.69 Hz, 1H), 3.84 (s, 3H), 3.73 (s, 3H). $^{13}$C NMR (100 MHz, CDCl$_3$) δ (ppm) 169.5, 169.0, 159.9, 151.6, 146.5, 135.3, 133.9, 131.2, 130.7, 130.2, 126.9, 1326.0, 125.1, 122.1, 118.2, 117.5, 114.6, 112.9. 96.4, 55.2, 51.9. ESI-MS m/z 412.0 [M+Na]$^+$.

Example 32

The following is an example of synthesis and characterization of a compound of the present disclosure. 3-((pyridin-2-yl)methylamino)-3-(4-methoxyphenyl)isobenzofuran-1 (3H)-one

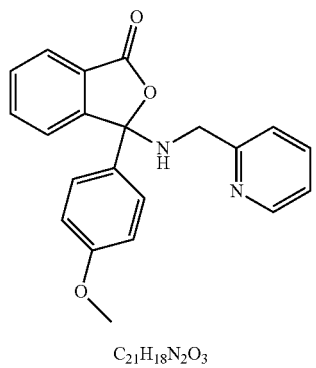

XH3094

C$_{21}$H$_{18}$N$_2$O$_3$
Mol. Wt.: 346.4

Yield 46.0%. $^1$H NMR (400 MHz, CDCl$_3$) δ (ppm) 8.44-8.42 (d, J=4.8 Hz, 1H), 7.79-7.77 (d, J=7.2 Hz, 1H), 7.74-7.71 (t, J=7.6 Hz, 1H), 7.53-7.50 (t, J=7.6 Hz, 1H), 7.45-7.42 (m, 4H), 7.35-7.33 (d, J=7.6 Hz, 1H), 7.24-7.22 (m, 1H), 6.89-6.88 (d, J=8.4 Hz, 2H), 5.06-5.02 (d, J=12.0 Hz, 1H), 4.19-4.15 (d, J=12.0 Hz, 1H), 3.80 (s, 3H). $^{13}$C NMR (100 MHz, CDCl$_3$) δ (ppm) 168.1, 159.6, 156.5, 147.9, 138.1, 132.9, 132.2, 129.4, 128.8, 127.8, 123.3, 122.9, 122.8, 122.6, 113.9, 90.4, 55.3, 44.6. ESI-MS m/z 369.0 [M+Na]$^+$.

Example 33

The following is an example of synthesis and characterization of a compound of the present disclosure. 3-(5-methyl-4-phenylthiazol-2-ylamino)-4-fluoro-3-p-tolylisobenzofuran-1 (3H)-one

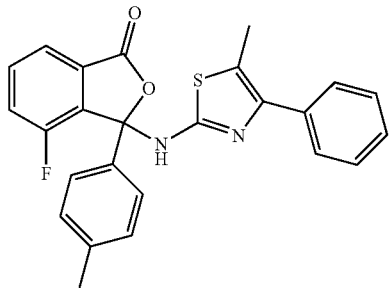

XH10165-1

C$_{25}$H$_{19}$FN$_2$O$_2$S
Mol. Wt.: 430.5

Yield 38.3%. $^1$H NMR (400 MHz, CDCl$_3$) δ (ppm) 7.80-7.78 (d, J=7.2 Hz, 1H), 7.56-7.51 (m, 1H), 7.43-7.41 (d, J=8.0 Hz, 2H), 7.40-7.35 (m, 4H), 7.32-7.30 (m, 1H), 7.26-7.21 (t, J=8.8 Hz, 1H), 7.16-7.14 (d, J=8.0 Hz, 2H), 2.51 (s, 3H), 2.31 (s, 3H). $^{13}$C NMR (100 MHz, CDCl$_3$) δ (ppm) 164.1, 158.4, 155.9, 152.0, 144.9, 138.5, 136.3, 134.4, 132.2 & 132.2 (1C), 131.3, 129.3, 128.3, 128.1, 127.5, 125.4, 122.3, 121.7, 121.5, 120.3, 92.9, 21.1, 12.3. ESI-MS m/z 431.0 [M+H]$^+$.

Example 34

The following is an example of synthesis and characterization of a compound of the present disclosure.

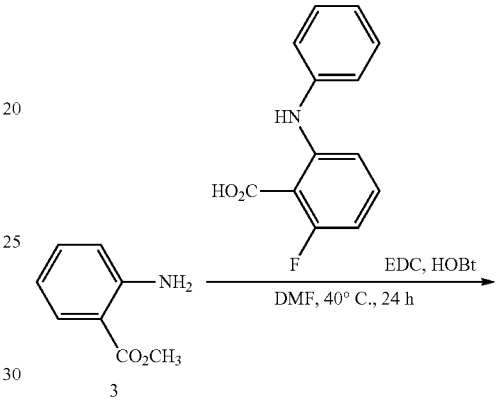

3

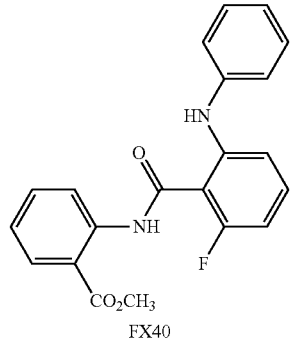

FX40

To a solution of compound 3 in DMF was added 2-fluoro-6-(phenylamino)benzoic acid, followed by EDC and HOBt. The reaction mixture was allowed to sit at 40° C. for 24 h, and then concentrated. After removing the solvent, the crude material was purified by flash column chromatograph to get the final compound.

REFERENCES

1. The Sabin Vaccine Institute: The Global Network. About NTDs. www.globalnetworkorg/2010
2. Hotez P J et al: Helminth infections: the great neglected tropical diseases. J Clin Invest 2008, 118(4):1311-1321. [PMID:18382743]
3. Rao A U, Carta L K, Lesuisse E, Hamza I: Lack of heme synthesis in a free-living eukaryote. Proc Natl Acad Sci USA 2005, 102(12):4270-4275. [PMID: 15767563]
4. Dutta S, Furuyama K, Sassa S, Chang K P: *Leishmania* spp.: delta-aminolevulinate-inducible neogenesis of porphyria by genetic complementation of incomplete heme biosynthesis pathway. Exp Parasitol 2008, 118(4):629-636. [PMID:18164705]

5. Rajagopal A et al: Haem homeostasis is regulated by the conserved and concerted functions of HRG-1 proteins. Nature 2008, 453(7198):1127-1131. [PMID:18418376]
6. Huynh C et al: Heme uptake by *Leishmania amazonensis* is mediated by the transmembrane protein LHR1. PLoS Pathog 2012, 8(7):e1002795. [PMID:22807677]
7. Miguel D C, Flannery A R, Mittra B, Andrews N W: Heme uptake mediated by LHR1 is essential for *Leishmania amazonensis* virulence. Infect Immun 2013. [PMID: 23876801]
8. Chatelain E, Ioset J R: Drug discovery and development for neglected diseases: the DNDi model. Drug Des Devel Ther 2011, 5:175-181. [PMID:21552487]
9. Smits H L: Prospects for the control of neglected tropical diseases by mass drug administration. Expert Rev Anti Infect Ther 2009, 7(1):37-56. [PMID: 19622056]
10. Mauel J: Vaccination against *Leishmania* infections. Curr Drug Targets Immune Endocr Metabol Disord 2002, 2(3):201-226. [PMID: 12476486]
11. Alvar J et al: The relationship between leishmaniasis and AIDS: the second 10 years. Clin Microbiol Rev 2008, 21(2):334-359, table of contents. [PMID: 18400800]
12. Markle W H, Makhoul K: Cutaneous leishmaniasis: recognition and treatment. Am Fam Physician 2004, 69(6): 1455-1460. [PMID: 15053410]
13. Cortes S, Afonso M O, Alves-Pires C, Campino L: Stray dogs and leishmaniasis in urban areas, Portugal. Emerg Infect Dis 2007, 13(9):1431-1432. [PMID: 18252134]
14. Desjeux P: The increase in risk factors for leishmaniasis worldwide. Trans R Soc Trop Med Hyg 2001, 95(3):239-243. [PMID: 11490989]
15. Jeronimo S M et al: An emerging peri-urban pattern of infection with *Leishmania chagasi*, the protozoan causing visceral leishmaniasis in northeast Brazil. Scand J Infect Dis 2004, 36(6-7):443-449. [PMID:15307565]
16. Landfear S M: Transporters for drug delivery and as drug targets in parasitic protozoa. Clin Pharmacol Ther 2010, 87(1):122-125. [PMID:19571801]
17. Hamza I, Dailey H A: One ring to rule them all: trafficking of heme and heme synthesis intermediates in the metazoans. Biochim Biophys Acta 2012, 1823(9): 1617-1632. [PMID:22575458]
18. Chang C S, Chang K P: Heme requirement and acquisition by extracellular and intracellular stages of *Leishmania mexicana amazonensis*. Mol Biochem Parasitol 1985, 16(3):267-276. [PMID:4058483]
19. Chang K P, Chang C S, Sassa S: Heme biosynthesis in bacterium-protozoon symbioses: enzymic defects in host hemoflagellates and complemental role of their intracellular symbiotes. Proc Natl Acad Sci USA 1975, 72(8): 2979-2983. [PMID:810795]
20. Croft S L, Seifert K, Yardley V: Current scenario of drug development for leishmaniasis. Indian J Med Res 2006, 123(3):399-410. [PMID: 16778319]
21. Yuan X, Protchenko O, Philpott C C, Hamza I: Topologically conserved residues direct heme transport in HRG-1-related proteins. J Biol Chem 2012, 287(7):4914-4924. [PMID:22174408]
22. White C et al: HRG1 Is Essential for Heme Transport from the Phagolysosome of Macrophages during Erythrophagocytosis. Cell Metab 2013, 17(2):261-270. [PMID: 23395172]
23. Shim J, Coop A, MacKerell A D, Jr.: Consensus 3D model of mu-opioid receptor ligand efficacy based on a quantitative Conformationally Sampled Pharmacophore. J Phys Chem B 2011, 115(22):7487-7496. [PMID: 21563754]
24. De Muylder G et al: A screen against *Leishmania* intracellular amastigotes: comparison to a promastigote screen and identification of a host cell-specific hit. PLoS Negl Trop Dis 2011, 5(7):e1253. [PMID:21811648]
25. Carvalho S et al: Heme as a source of iron to *Leishmania infantum* amastigotes. Acta Trop 2009, 109(2):131-135. [PMID:19013419]
26. Spath G F, Beverley S M: A lipophosphoglycan-independent method for isolation of infective *Leishmania* metacyclic promastigotes by density gradient centrifugation. Exp Parasitol 2001, 99(2):97-103. [PMID: 11748963]
27. Jain S K, Sahu R, Walker L A, Tekwani B L: A parasite rescue and transformation assay for antileishmanial screening against intracellular *Leishmania donovani* amastigotes in THP1 human acute monocytic leukemia cell line. J Vis Exp 2012(70). [PMID:23299097]

What is claimed is:
1. A compound having the following structure:

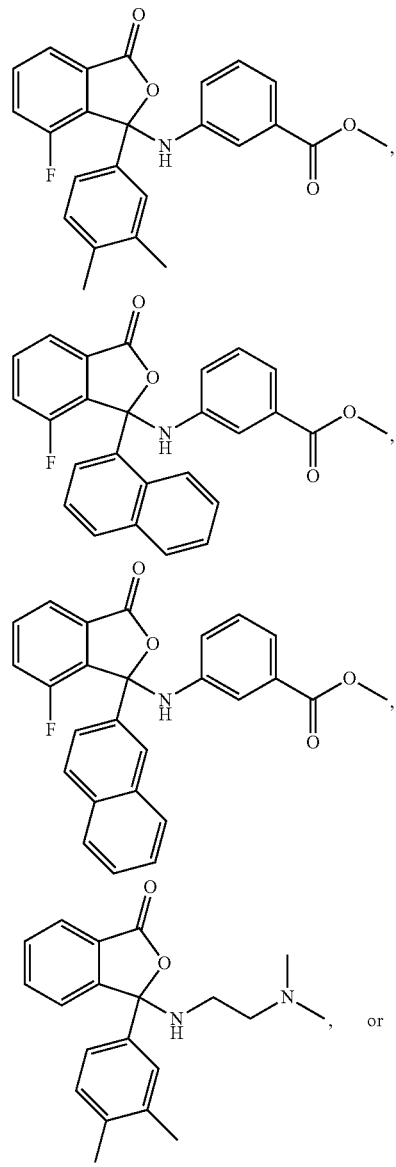

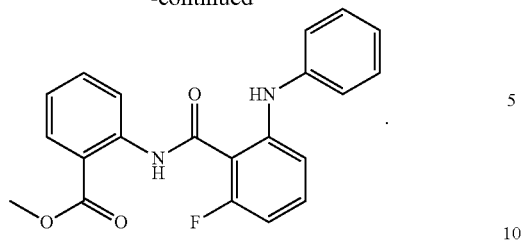
2. A composition comprising one or more compounds of claim 1.
* * * * *